US009301887B2

(12) United States Patent
Coates

(10) Patent No.: US 9,301,887 B2
(45) Date of Patent: Apr. 5, 2016

(54) PROTECTIVE UNDERGARMENT USING IMPROVED HOOK AND LOOP FASTENERS

(75) Inventor: Frederica V. Coates, Winston-Salem, NC (US)

(73) Assignee: Tailored Technologies, Inc., Winston-Salem, NC (US)

( * ) Notice: Subject to any disclaimer, the term of this patent is extended or adjusted under 35 U.S.C. 154(b) by 244 days.

(21) Appl. No.: 13/809,654

(22) PCT Filed: Jul. 12, 2011

(86) PCT No.: PCT/US2011/043710
§ 371 (c)(1),
(2), (4) Date: Mar. 19, 2013

(87) PCT Pub. No.: WO2012/009357
PCT Pub. Date: Jan. 19, 2012

(65) Prior Publication Data
US 2013/0172844 A1 Jul. 4, 2013

Related U.S. Application Data

(60) Provisional application No. 61/399,472, filed on Jul. 12, 2010.

(51) Int. Cl.
*A61F 13/15* (2006.01)
*A61F 13/49* (2006.01)
*A61F 13/505* (2006.01)
*A61F 13/56* (2006.01)
*A61F 13/62* (2006.01)
*A61F 13/539* (2006.01)

(52) U.S. Cl.
CPC ..... *A61F 13/49004* (2013.01); *A61F 13/15268* (2013.01); *A61F 13/505* (2013.01); *A61F 13/5633* (2013.01); *A61F 13/622* (2013.01); *A61F 2013/53983* (2013.01)

(58) Field of Classification Search
CPC .................. A61F 13/49003; A61F 13/49004; A61F 13/505; A61F 13/622; A61F 13/625; A61F 13/627; A61F 2013/5055; A61F 2013/53983; A61F 13/15268; A61F 2013/15276
USPC ................... 604/385.14, 385.15, 385.19, 391
See application file for complete search history.

(56) References Cited

U.S. PATENT DOCUMENTS 4,680,030 A 7/1987 Coates et al.
5,069,672 A * 12/1991 Wippler et al. .......... 604/385.14
(Continued)

FOREIGN PATENT DOCUMENTS

WO 2007021734 A2 2/2007

OTHER PUBLICATIONS

International Search Report for PCT/US2011/043710 dated Dec. 23, 2011.

*Primary Examiner* — Lynne Anderson
(74) *Attorney, Agent, or Firm* — Shumaker, Loop & Kendrick, LLP

(57) ABSTRACT

A protective undergarment includes a sling that is suspended from an outer shell. The sling forms a pocket in which a reusable or disposable absorbent pad can be positioned. The sling has arcuate, stitched end edges at both the front and the rear of the sling. The garment thus fits better will less chance that portions of the sling at opposite ends of the pocket will be exposed to moisture. The sling can also be attached to and detached from the garment by using hook and loop fasteners that can be partially covered so that abrasive corners are not exposed. The same overlying layers can be used on tabs for securing the protective undergarment around the waist.

6 Claims, 25 Drawing Sheets

(56) References Cited

U.S. PATENT DOCUMENTS

| | | | |
|---|---|---|---|
| 5,325,543 A * | 7/1994 | Allen | 2/406 |
| 5,360,422 A * | 11/1994 | Brownlee et al. | 604/385.15 |
| 6,575,951 B1 * | 6/2003 | Ono et al. | 604/385.14 |
| 8,216,201 B2 * | 7/2012 | Beck | 604/385.14 |
| 2002/0143316 A1 * | 10/2002 | Sherrod et al. | 604/385.101 |
| 2003/0009144 A1 | 1/2003 | Tanzer et al. | |
| 2003/0216705 A1 | 11/2003 | Coates | |
| 2005/0125879 A1 | 6/2005 | Yang et al. | |

* cited by examiner

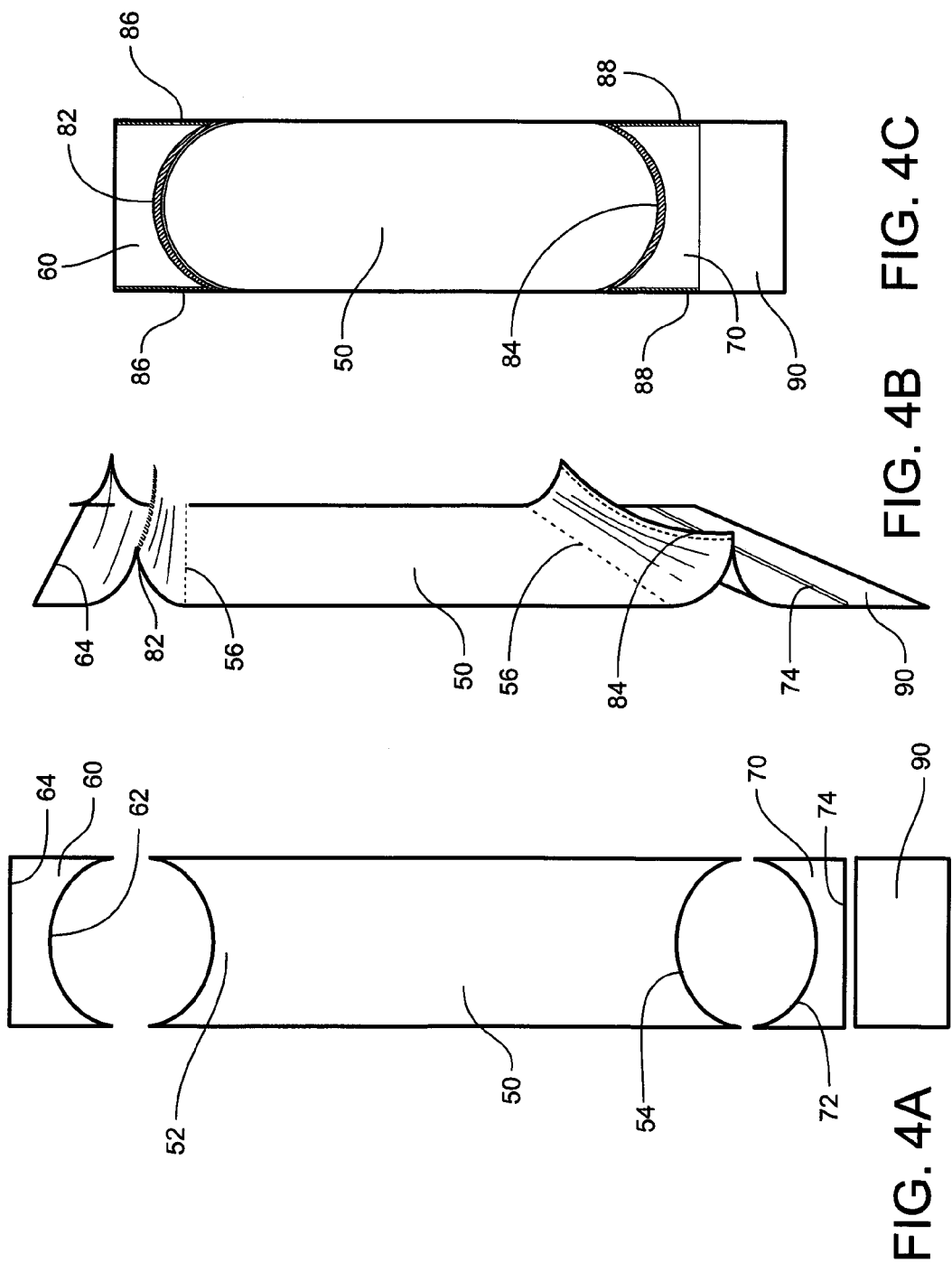

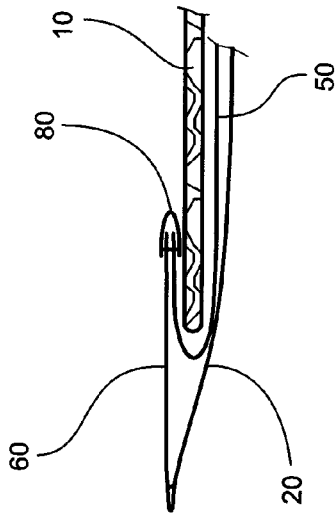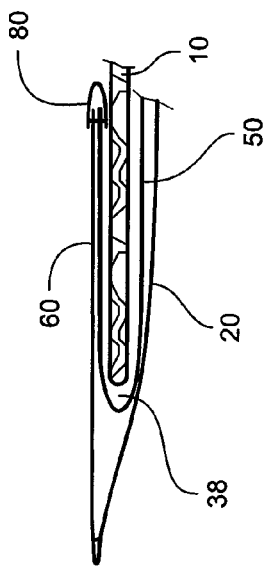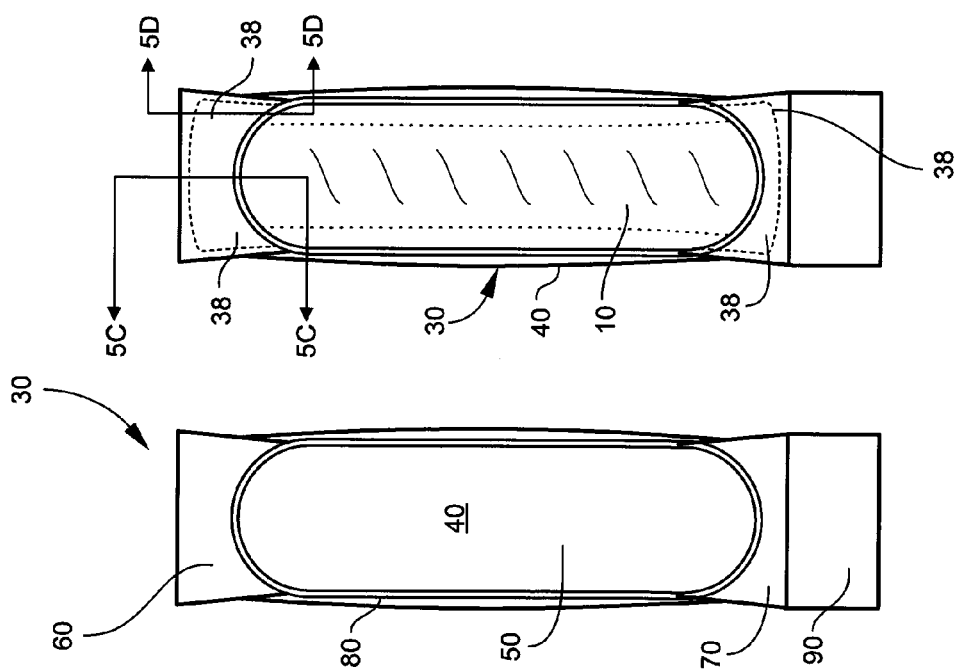

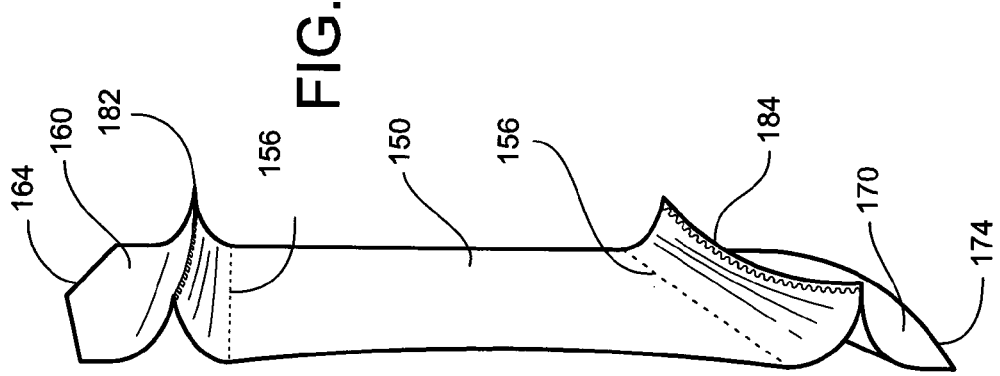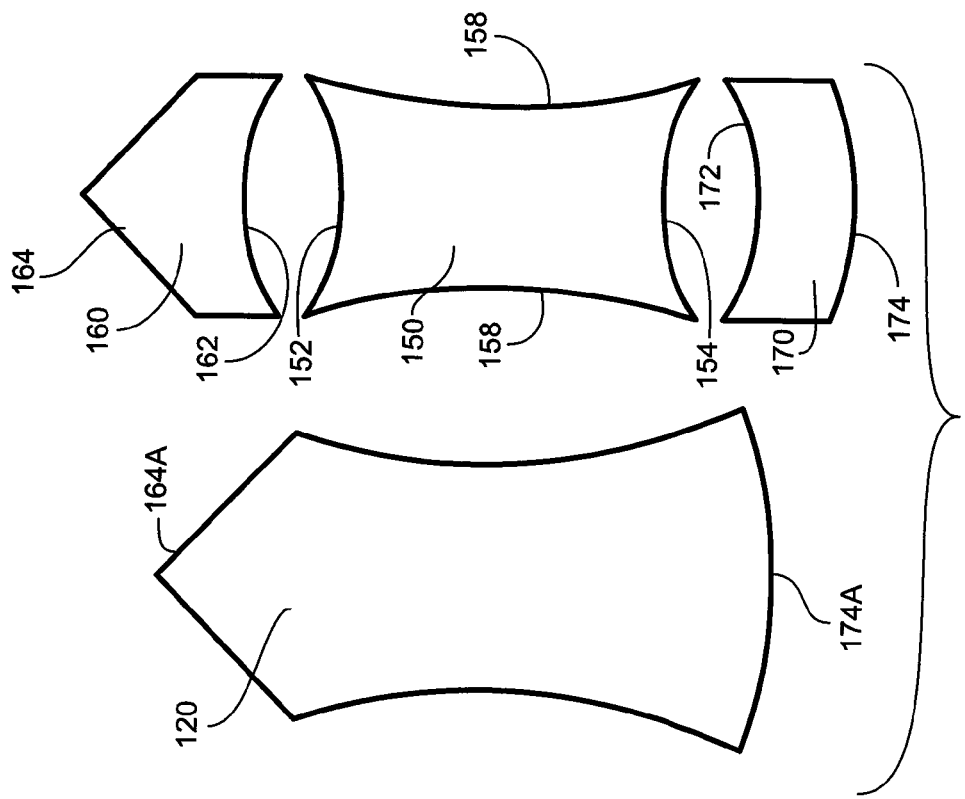

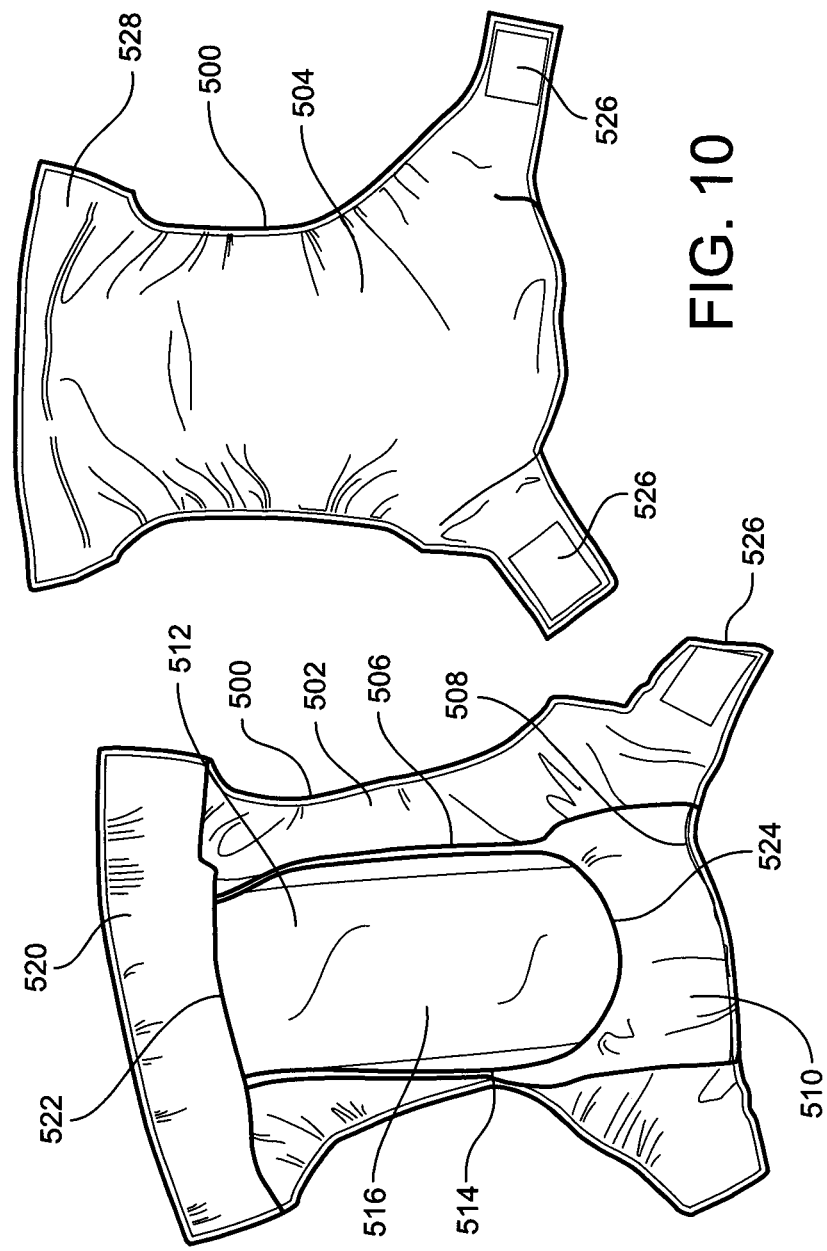

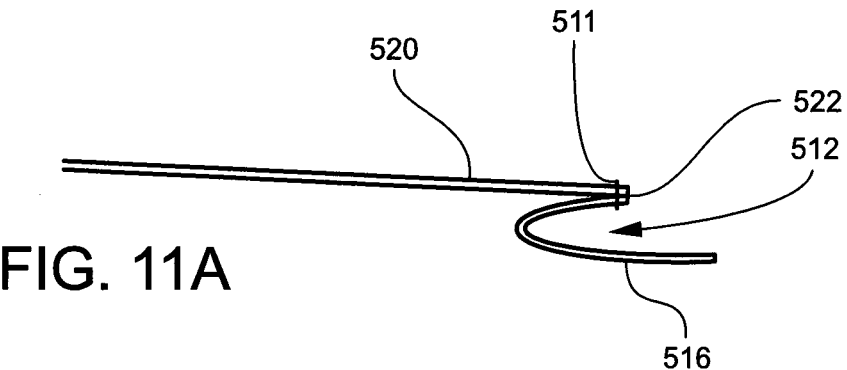
FIG. 11A
FIG. 12
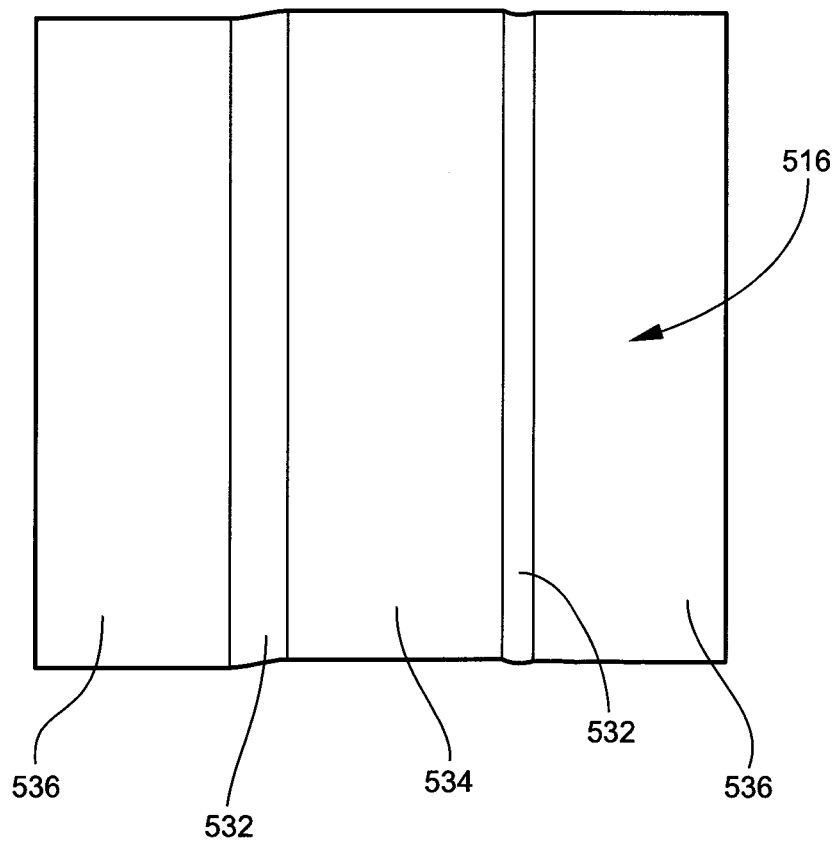

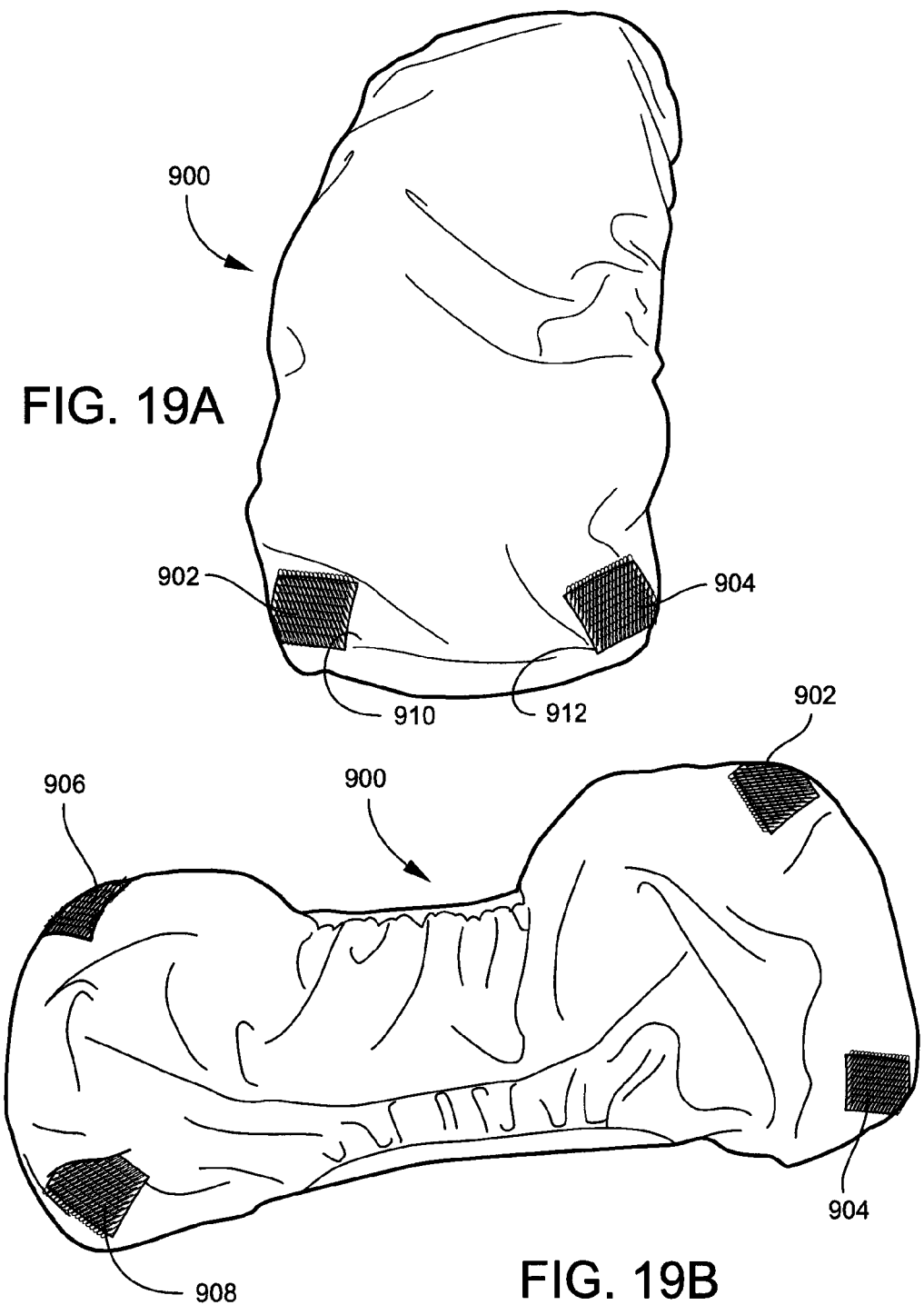

PROTECTIVE UNDERGARMENT USING IMPROVED HOOK AND LOOP FASTENERS

BACKGROUND

This invention relates to protective undergarments that can be constructed in different sizes, and which may be used by adults and children.

Protective underwear having a waterproof or water-resistant sling is shown in U.S. Pat. No. 5,137,526; U.S. Pat. No. 5,409,476; U.S. Pat. No. 5,707,364; U.S. Pat. No. 6,254,583; U.S. Pat. No. 5,722,127; U.S. Pat. No. 6,895,603; and U.S. Pat. No. 6,926,705. U.S. Pat. No. 5,814,037 shows a protective undergarment with a releasable pocket-sling. Front and rear ends of these slings are joined to an outer shell so that the sling can isolate body fluids and fecal matter from the outer shell. A suspended pocketed sling shown in U.S. Pat. No. 6,895,603 is formed by folding front and rear sections of a rectangular fabric about fold lines extending transverse to the major or longitudinal dimension of the rectangular fabric, so that overlapping portions of the rectangular fabric form fore and aft pockets. Exterior crease lines are covered by an elastic trim. Elastic is also placed along side edges to recess and cup the entire frontal portion of the sling to better fit the wearer's anatomy. Stitching along the edges of the pocket holds the three plies of the S-folded fabric construction together. A rectangular pocket opening is thus formed by the transverse fold lines and the longitudinal edges of the rectangular fabric. Remote ends of this pocketed sling can then be attached or stitched to the outer shell, which may be in the form of a pant or a diaper. The sling can hang freely from the opposite ends of the garment, and the absence of stitching between the sling and the garment in the area of the pocket eliminates a leakage path. A disposable pad, either reusable or disposable can be fitted in the pocket, with the ends of the pad held by the fore and aft overlapping or S-shaped sections at opposite ends of the rectangular pocket opening. Although this rectangular pocket can provide a pocket of sufficient volume to collect bodily wastes, and an absorbent pad can be held in place within the pocket, the rectangular opening does not naturally conform to pubic area of the wearer. The exposed material along the crease lines formed by the transverse fold can become soiled compromising the effectiveness of the protective undergarment. This is especially a problem along the front of the undergarment when used for males, especially small boys, because the straight edge of the rectangular opening is wets easily.

In some prior art undergarments formed with S-pockets having rectangular edges, elastic encircles the rectangular sling opening. This elastic pulls material inward and can cause the pocket opening to take on an oval shape with curved front and rear openings. However, this effect of the elastic reduces the size of the pocket opening and provides less, not more, exposure of a disposable pad. This effect thus exposes more of the layer of the sling adjacent to the wearer to the pubic area and increases the area that can be wetted, especially for males. This ovaling effect thus reduces the effectiveness of S-pocket garments formed by a rectangular fold line.

U.S. Pat. No. 5,707,364 discloses another type of recessed pocket, in which a replaceable pad may be positioned. FIG. 17 is a view of a diaper constructed in accordance with the teachings of this patent. The recessed pocket formed in FIG. 17 according to U.S. Pat. No. 5,707,364 includes drop strips 8A(PA) on either side of the pocket. These drop strips 8A(PA) provide depth to the pocket and they are stitched to an absorbent channel 16A(PA) at the base of the drop strips. As disclosed in U.S. Pat. No. 5,707,364, the absorbent pads fit between the drop strips 8A(PA), and it is the added depth that is primarily relied upon to retain the removable absorbent pads in place. Some embodiments depicted therein include elastic strips extending over the pads between the drop strips 8A(PA) to provide additional restraint. A bumper strip 14(PA) extends across the front of the sling 8(PA), and that sling is free to float relative to the outer shell of the protective undergarment or diaper shown therein. The sling 8(PA), formed by the drop strips 8A(PA), and the channel 16A(PA) are joined to the bumper 14(PA) by an arcuate seam 82A (PA). U.S. Pat. No. 5,707,364 refers to this as recessing and pocketing, but the pocket referred to therein is in the middle of the sling 8A(PA), and not at its ends. there is no pocket above the arcuate seam 82A(PA), because that seam, as shown in FIG. 17, extends through both the drop strips 8A(PA) and the channel 16A(PA). Thus there is no S-pocket formed above seam 82A(PA) for receiving or retaining an end of a disposable pad either at the front or rear of the garment, nor does the arcuate seam 82A(PA) provide a capability to retain a pad of any kind.

SUMMARY

According to this invention, a protective undergarment can include an outer member conforming to the waist and groin of a wearer, a detachable pocket member and an absorbent pad retained by the pocket member. The pocket member can be attached to and detached from the outer member. A hook or loop fastener is located at each corner of the pocket member. The outer member includes complementary loop or hoop fasteners that can be attached to and detached from the hook or loop fastener members on the pocket member. Corners of the fasteners can also be covered by folding material over the sides of the fasteners before stitching the folds to the fasteners.

According to another aspect of this invention, a protective undergarment includes an outer garment conforming to the waist and groin of a user. The outer garment includes a tab located at corners of one end of the outer garment. The tab includes a hook fastener, with overlying folds extend over each of four hook fastener corners so that hook fastener corners are not exposed to the wearer. An adjacent loop fastener provides means for securing the hook fastener when not in use, for example when the diapers are washed. A shrinkable material, such as cotton between the hook and loop tab fasteners helps secure the tab hook fastener to the tab loop fastener.

BRIEF DESCRIPTION OF THE DRAWINGS

FIGS. 4A-4C are views showing the fabrication of the sling from individual fabric pieces for use in the protective undergarment of FIGS. 1-3;

FIGS. 5A-D show the completion of the sling pocket and the manner in which an absorbent pad can be retained in the pocket with arcuate end edges;

FIG. 7A show the separate component parts of a sling employed in the embodiment shown in FIG. 6;

FIG. 7B is a perspective view showing and intermediate step in the fabrication of the sling from components shown individually in FIG. 7A;

FIG. 9 is a view of the interior of another version of this invention. This embodiment limits the tendency of the front edge of the undergarment to roll inward and irritate the wearer's skin;

FIG. 10 is a view of the exterior of the protective undergarment of FIG. 9;

FIG. 11A is a view taken along section lines 11A-11A in FIG. 11 showing the S-pocket configuration formed at the front of the sling. This view is not to scale, so that smaller features may be seen, and therefore the arcuate edge and seam are smoother than may appear in this view;

FIG. 12 is a view of a tri-fold, multi-layer absorbent pad that can be employed in this invention;

FIGS. 19A and 19B show a sling employing hook fastener tabs, generally attached as in FIGS. 17A-17G, are employed at each corner of the sling.

DETAILED DESCRIPTION OF EMBODIMENTS

Figure 1:
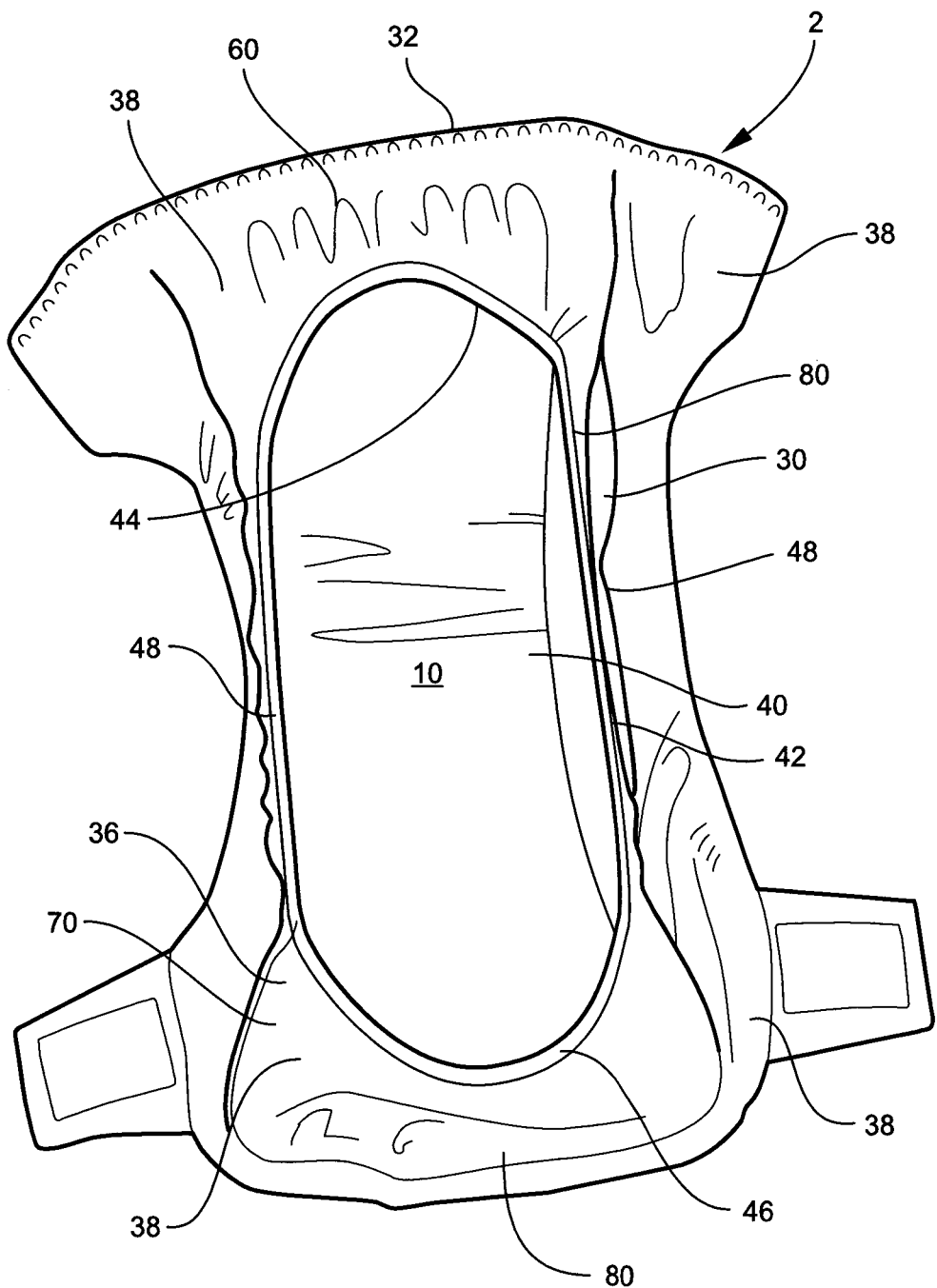
FIG. 1 is a view of a first embodiment of a protective undergarment according to this invention showing an absorbent pad disposed within a sling having end pockets with arcuate openings.
Figure 2:
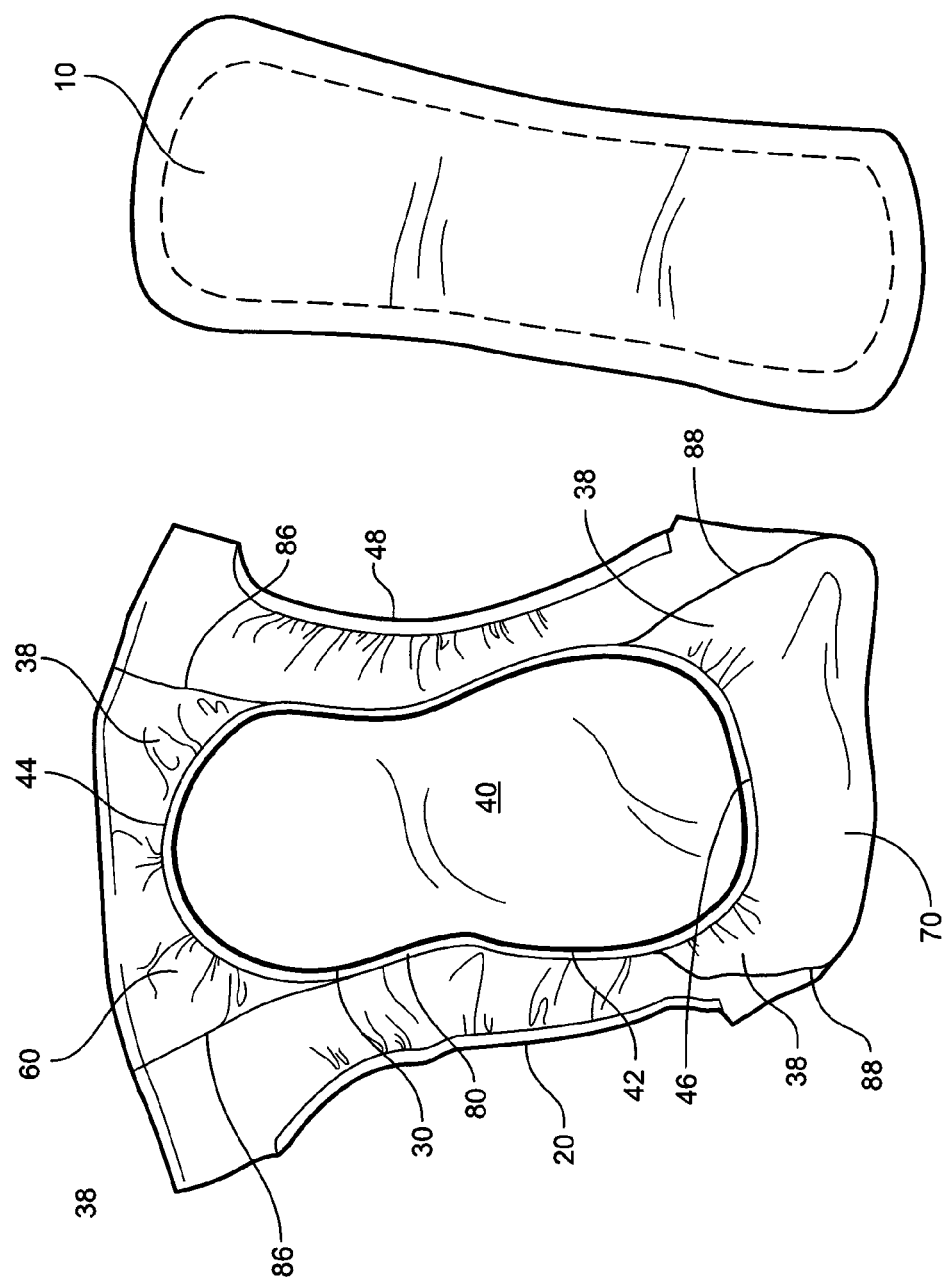
FIG. 2 is a view of the protective undergarment shown in FIG. 1 showing the absorbent pad removed from the sling pocket.
Figure 3:
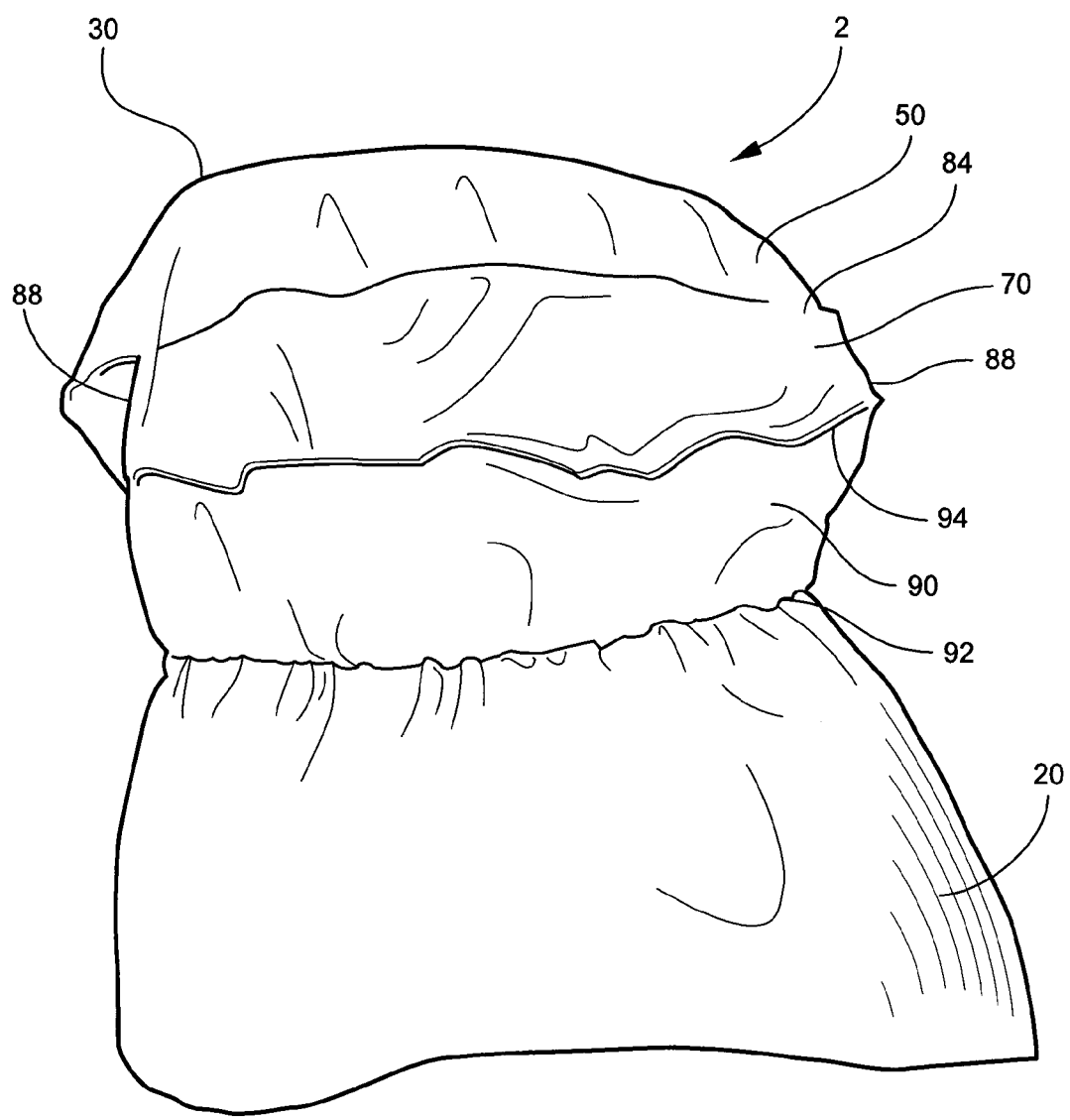
FIG. 3 is a view of the protective undergarment of FIGS. 1 and 2 in which the sling is folded relative to the outer shell to expose seams between sections of the sling.

The first embodiment of the protective undergarment 2, shown in FIGS. 1-3 is a reusable diaper, which includes an outer fabric shell 20 with an inner sling 30 extending between front and a rear of the outer shell 20. The sling 30 forms a pocket 40 in which a reusable or a disposable absorbent pad 10 is retained so that the absorbent pad 10 will be adjacent the wearer's pubic area. Unlike other protective undergarments, the pocket 40 has arcuate end edges 44 and 46 at both ends to form a pocket opening 42 in which the exposure of the absorbent pad 10 is increased to limit soiling of the sling 30 and the outer shell 20. The pocket opening 42 with arcuate end edges 44 and 46 has been found to conform better to the wearer's anatomy so that portions of the sling fabric adjacent to a longitudinal centerline of the sling and pocket will not be soiled as has occurred with prior art protective undergarments, which have straight edges on one or both ends of the sling pocket. In addition to increasing the exposure of the absorbent pad 10 in areas likely to be soiled, this embodiment also eliminates seams between the sling 30 and the outer fabric shell 20 in the vicinity of the pocket 40 and the absorbent pad 10 where fluid leakage paths formed by the seams could otherwise cause problems.

Although the arcuate pocket end edges 44, 46 expose the absorbent pad 10, four corner pocket sections 38 will retain corners of the absorbent pad 10 securely within the pocket 40. These four corner pocket sections 38 are formed of multiple layers of fabric pieces bordered by the arcuate end edges 44, 46. The construction of these corner pocket sections 38 will be subsequently described in greater detail. Furthermore, these arcuate end edges 44, 46 together with the generally parallel pocket side edges 48 form a pocket opening 42, on the inner sling face 36, allowing the absorbent pad to be easily inserted into the pocket 40. A soiled pad 10 can be easily extracted since the user can grasp unsoiled portions of the absorbent pad 10 along its edges. An elastic trim 80 extending completely around the pocket opening 42 provides additional retention.

Fabrication of the protective undergarment 2, shown in FIG. 1-3 is demonstrated in FIGS. 4A-C, and in FIGS. 5A-B. FIG. 4B shows a first step in the fabrication of an inner sling 30 from the individual fabric pieces shown in FIG. 4A. These fabric pieces include a central fabric section 50, a fore fabric section 60, and aft fabric section 70 and an intermediate section 90, which has a greater elasticity than the other fabric sections. Preferably, the fabric sections used to form the sling 30 are formed from a generally waterproof or water resistant material, such as commercially available materials, with the exception of the intermediate section 90, which can be formed of an elastic material, such as commercially available materials.

The central fabric section 50 is cut to form a first concave edge 52 and an opposite second concave edge 54. In the preferred embodiment, these concave edges 52, 54 have a generally constant radius of curvature, substantially equal to the radius of curvature to be formed as pocket end edges 44, 46. It should be understood however, that this arcuate contour need not have a constant radius of curvature, and that other embodiments can be adopted.

The fore fabric section 60 can be shorter than the central fabric section 50 and has a fore concave edge 62 and a fore upper edge 64, which in this embodiment is in the form of a straight line, which will extend perpendicular to the longitudinal centerline of the sling 30. As will be described with respect to other embodiments, this upper edge 64 need not be straight when the invention is employed with other protective undergarments. The arcuate contour of the fore concave edge 62, should, however conform to the fore concave edge 52 of the central fabric piece 50, because these two arcuate edges will be stitched together to form the sling 30.

The shape of the aft fabric section 70 can be generally the same as the shape of the fore fabric section 60, although its length can be different, because this aft section 70 can be attached to the intermediate piece 90, which in turn will be attached to the other shell adjacent the sling rear end 34. The contour of the aft concave edge 72 conforms to the concave contour of the rear arcuate edge 54 to which it will be stitched. Although the aft upper edge 74 can have different shapes, it will normally be straight since it will be stitched directly to the intermediate piece 90, which will form a generally elastic spacer between the remainder of the sling 30 and the outer shell 20 to which it will be stitched or otherwise attached.

The fabric pieces shown in FIG. 4A will be stitched or otherwise attached together in the order shown in FIG. 4B as part of the first step in the fabrication of the sling 30. FIG. 4B shows all of these pieces stitched together end to end. The central fabric concave edges 52 and 54 are stitched to the corresponding fore and aft concave edges 62, 72 to form an arcuate front seam 82 and an arcuate rear seam 84. The intermediate piece 80 is stitched to the aft fabric piece 70 along a straight steam 94.

The next step in the fabrication of the sling 30 is to fold the central fabric piece 50 about transverse fold lines 56 located adjacent to and inward of the arcuate seams 82 and 84. FIG. 4C shows the resultant structure in which overlapping corner pockets or sections 38 are formed at each of the four corners of the pocket opening 42. The fore and aft fabric sections 60 and 70 will now overlap portions of the central fabric section between the fold lines 56 and the seams 82 and 84, as well as central fabric portions inboard of the fold lines 56. A three layer construction or a S-shaped pocket will be formed, with overlapping sections in the corners having a greater longitudinal depth than nearer the longitudinal centerline of the sling 30. These corner pockets 38 are completed by side edge seams 86 and 88, which extend from the arcuate seams 82, 84 to the fore and aft upper edges 64, 74.

FIG. 5A shows completion of the pocket 40 by addition of the elastic trim 80 around the pocket opening 42. This elastic trim 80 will be stitched over the arcuate seams 82 and 84, and will extend along the pocket side edges 48, so that the elastic trim 80 will be in a position to trap or retain an absorbent pad 10 inserted into the pocket 40 as shown in FIG. 5B. In the preferred embodiment, this elastic trim can be a single piece with a first end attached adjacent the intersection between one of the side seams 86 or 88 and the corresponding arcuate seam 82 or 84.

The sling 30 can now be stitched to the outer shell 10 along the sling front end 32 and the sling rear end 34. The upper edge 64 of the fore fabric section 60 will be stitched directly to the outer shell 20, and the relatively elastic intermediate piece, attached to aft fabric section 70, will be stitched to the rear of the outer shell. In the preferred embodiment, the sling 30 will be attached to the outer shell 20 only along these ends with no intermediate seams. There will then be no leakage paths formed along and seams in the vicinity of section of the pocket 40 in which an absorbent pad 10 will be disposed.

Figure 6:
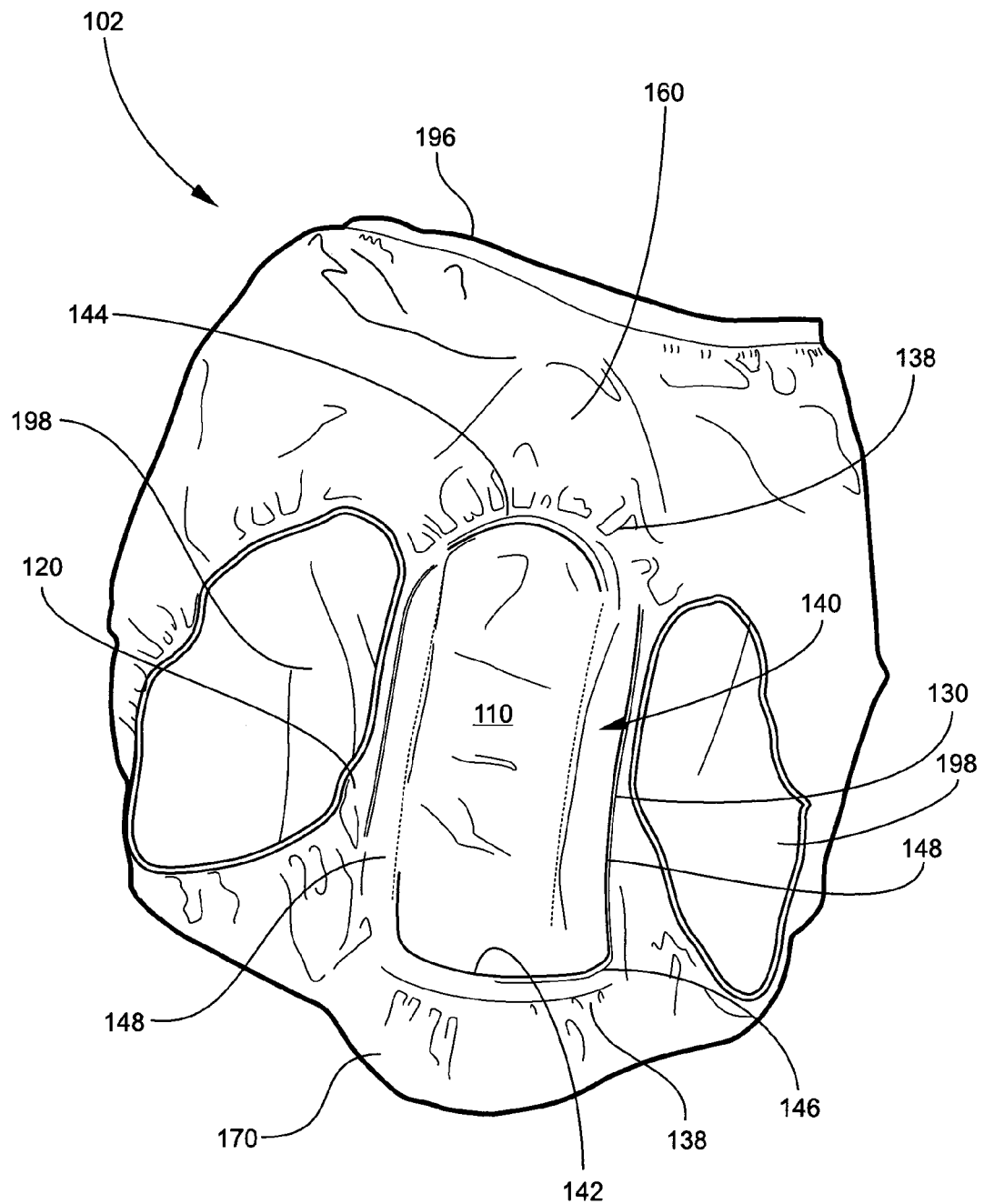
FIG. 6 is a view of an alternate embodiment of this invention in which a sling with arcuate ends is used in a lady's panty.

Another alternate embodiment of this invention is shown in FIGS. 6 and 7A-B. FIG. 6 show a panty 102 that is reversed to show the interior of the panty on which an absorbent pad 110 will be positioned. This embodiment is in the form of a lady's panty 102, that is specially suited as a protective undergarment, which is compatible with the female anatomy. In this embodiment a sling 130 and a shell 120, which forms the crotch portion of the lady's panty 102, are both stitched or otherwise attached to what is substantially otherwise a conventional lady's panty. Both the outer shell 120 and the sling 130 are preferably fabricated from a liquid or waterproof or resistant material. The remainder of the panty can be fabricated from a conventional material or materials normally used in a standard lady's panty or other undergarment. For example, a conventional disposable pad has a waterproof covering on the back. The pocket for a lady's protective undergarment according to this invention could then be fabricated from a non waterproof or non water resistant material, such as a cool mesh material. The remainder of the panty can be fabricated from a conventional material or materials normally used in a standard lady's panty or other undergarment.

One significant difference between the configuration shown in FIG. 6 and that employed in the embodiment of FIGS. 1-3 is the shape of the fore fabric section 60 and the rear fabric section 170. The fore fabric section 160 has an upper edge 164 that is formed by two intersecting upper edges instead of the right angle edge 64 in the first embodiment. The rear fabric section 170 has a curved or arcuate lower edge 174 instead of the straight edge 74 in the first embodiment. The sling 130 and outer shell 120 are also largely confined to the crotch area and do not extend to the waistband 196. The sling 130 extends between the leg openings 198 and elastic along the sides of the outer shell 120 will form a part of these leg openings 198 on either side of the sling 130.

The central sling fabric section 150 has the same basic shape as the central fabric section 50 in the first embodiment, although of course the dimensions need not be the same. The front edge 152 and the rear edge 154 are also concave and arcuate as in the earlier embodiment. In this embodiment the side edges 158 can also be slightly curved to insure a better fit. The fore fabric section 160 has an arcuate concave inner edge 162 and an upper edge 164 formed by two intersection edges so that this waterproof or resistant section can extend upwardly to provide a sufficient barrier. Lower fabric section 170 has an upper arcuate concave edge 172 and a convex edge 174, which will be attached directly to the fabric forming the major portion of the lady's panty. The curvature of the arcuate edges 162 and 172 is substantially the same as the curvature of the arcuate ends 152 and 154 on the central fabric section 150. As shown in FIG. 7B, these arcuate edges on fabric sections 150, 160 and 170 will be stitched together along seams 182 and 184 and this subassembly will be folded along fold lines 156 to form a sling 130 in the same trimmer as in the earlier embodiment of FIGS. 1-3. Seams (not shown) are formed along the sides of the fore fabric section 160 and the aft fabric section 170 in the same manner as in the first embodiment. The remote edges 164 and 174 of fore fabric section 160 and rear fabric section 170 respectively will be stitched to edges 164A and 174A, and in turn stitched to the remainder of the panty adjacent the upper and lower edges of the leg openings 198.

The pocket 140 formed by sling 130 is quite similar to that of the first embodiment, with of course extra room being formed at the apex of the top edge 164 of the fore fabric section 160. However, this additional space in the pocket does not provide extra retention for an absorbent pad 110 having the same shape as pad 10. Corner pocket sections 138 at both the front and rear ends still provide the primary retention for a pad 110 inserted in the pocket 140. The pocket opening 142 has the same shape as the pocket opening 42 with arcuate sections 144 and 146 at the front and rear of the pocket opening 142. The pocket side edges are substantially straight and an elastic trim extends around the pocket opening 142 in the same manner as in the first embodiment.

Figure 8:
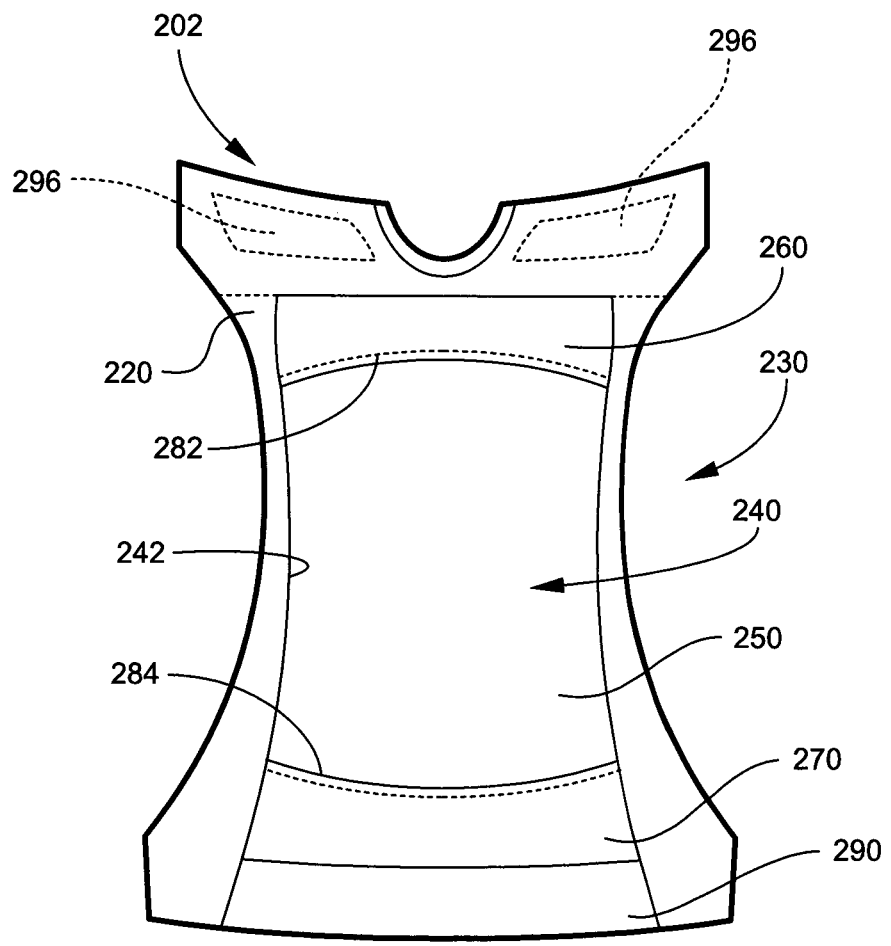
FIG. 8 shows a third embodiment of a protective undergarment as a partially completed configuration.

A third embodiment, shown in FIG. 8, is even simpler than the first two embodiments. The protective undergarment 202 is shown at a stage prior to complete fabrication of the undergarment. To complete the protective undergarment 202, elastic trim can be added around the pocket opening 242, as in the other embodiments, and elastic straps will be attached to opposite sides of the rear of shell 220, so that these straps will extend around the wearer's waist to hold the garment in place. Loop fasteners on these straps (not shown) can then be attached to hook fasteners 296 on the outside of the shell 220. The sling 230 is formed of a central fabric segment 250, a fore fabric segment 260 and an aft fabric segment 270, which is in turn attached to a relatively more elastic intermediate section 290, which will be secured to the rear of the shell 220. Arcuate end edges 282 and 284 are formed on the front and rear of the pocket 240 in substantially the same manner as in the first two embodiments. The pocket 340 is formed in the same manner as in the earlier embodiments. An absorbent pad can then be inserted into the pocket 240 where it will be primarily held in place along the corners of the absorbent pad, in the same manner as in the earlier embodiments.

Figure 16:
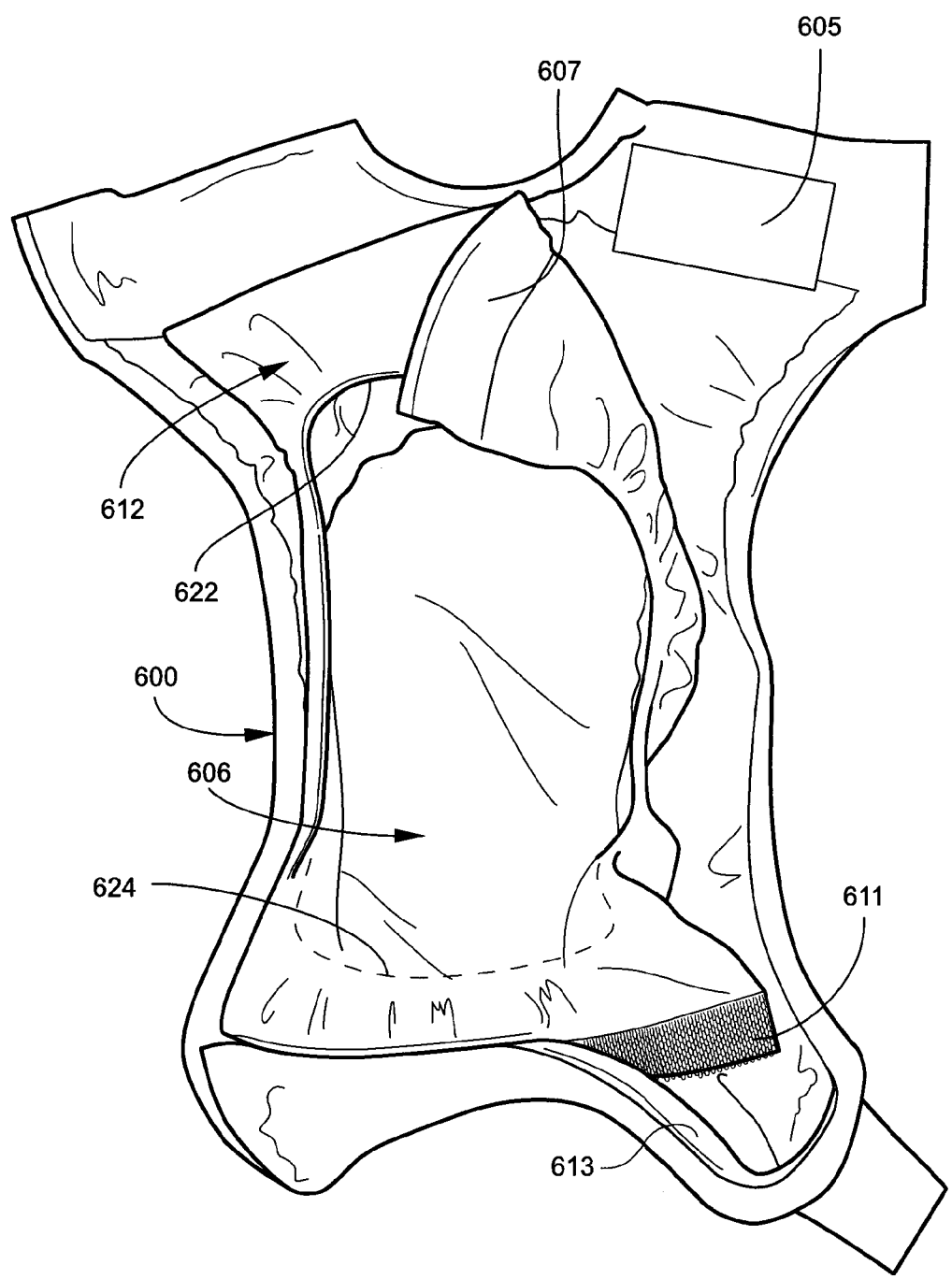
FIG. 16 is a view of another embodiment of the protective undergarment in which the sling is detachable from the outer shell.

Another embodiment of this invention is shown in FIG. 16. This protective undergarment 600 includes a detachable pocket sling 606 that has pockets 612 for retaining an absorbent pad. The edges 622 and 624 are arcuate to provide maximum exposure of the absorbent pad, and these arcuate edges 622 and 624 are formed in the same manner as earlier embodiments. The pockets receiving the ends of the absorbent pads are still S-shaped. The sling 606 can be detached from the outer shell of this garment. In FIG. 16, one side of the sling 606 remains attached to the outer shell, while on the other side edge, complementary fasteners are show in a disengaged position. At the front of the protective garment, complementary hook and loop fasteners 605 and 607 can be used to attach the sling 606 to the outer shell. Of course these fasteners can be disconnected. Therefore when slings are referred to as being attached to the outer shell, it should be understood that attached can be interpreted as permanently attached, as by stitching, or releasably attached as with this embodiment or by using snaps instead of hook and loop fasteners. Complementary hook and loop fasteners 611 and 613 are also located at the rear of the protective undergarment 600. Fastener 611 on the sling faces inwardly, away from the outer shell. Fastener 613 is located on a hidden surface of a cuff or fabric strip so that fastener would face away from the wearer, and the cuff or fabric strip would remain between the wearer and the fastener protecting the wearer from abrasive fasteners.

Another embodiment of a protective undergarment 500 is shown in FIGS. 9 and 10. This undergarment is intended to prevent potentially abrasive hook and loop fasteners from coming into contact with the sensitive skin of the wearer. In this representative embodiment, the outer shell of the diaper comprises a soft inner fluid absorbent layer 502 stitched along peripheral edges to an outer fluid resistant or waterproof layer 504. A sling 506 is suspended from opposite ends of the undergarment 500, and the sling 506 is free to float between these two opposite ends. The sling 506 is preferably fabricated from a fluid resistant or waterproof material. There are no stitches directly connecting the sling 506 with the inner fabric layer 502, and therefore there are no potential leakage paths formed along connecting seams.

The rear portion of the sling 506 is joined at the rear edge 508 of the shell by an intervening fluid resistant section 510, in the same fashion as in the embodiment of FIG. 1.

An elastic trim 514 extends partially around the inner edge of the sling 506 to form a pocket 512 into which an absorbent pad 516 may be introduced and removed when soiled. The elastic trim 514 does not however extend around the front edge of the pocket 512, where the sling 506 is joined to the outer shell by a fabric strip 520 that extends between opposite sides of the undergarment 500. The edge 522 where the sling 506 is joined to the fabric strip 520 is still arcuate so that both the front and rear ends of the pocket conform to the wearer's pubic area and provide maximum exposure of the absorbent pad 516 to the wearer so that the remainder of the protective undergarment 500 will not be soiled.

Figure 11:
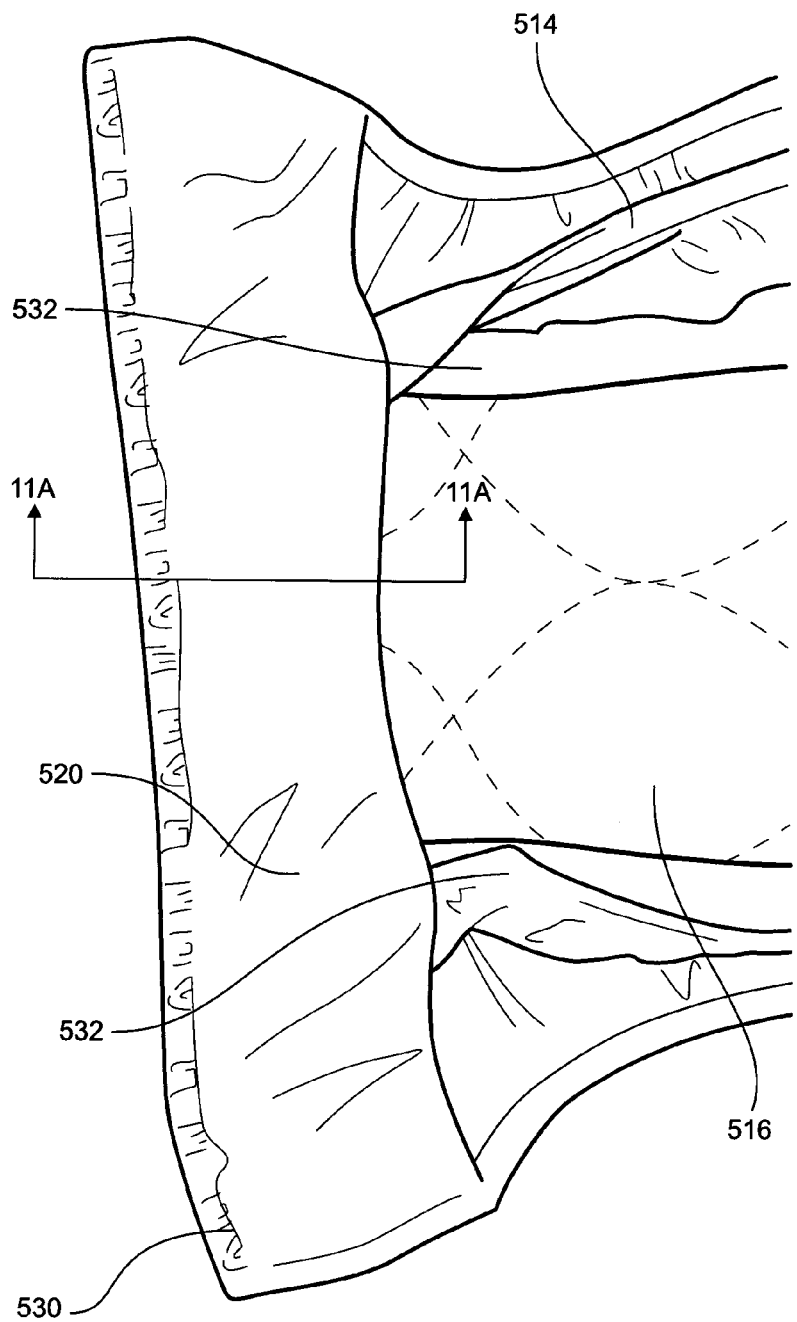
FIG. 11 is an enlarged view of the front edge of the protective undergarment of FIGS. 9 and 10.

A stitched seam connects the sling 506 to the fabric strip 520, and this arcuate shaped seam extends between opposite sides of the undergarment 500. In the center of this arcuate seam, the top edge of the fabric forming the sling 506 is stitched to the fabric strip 520. At the edges of the front edge of the sling 506, the sling is overlapped to form the pocket 512 and to define the corners that will retain the front edge of the absorbent pad 516 in place. The fabric strip 520 is on an opposite face of the undergarment 500 from the front fastener strip 528, which extends along between sides of the outer fabric 504 as shown in FIG. 10. As shown in FIGS. 10 and 11 a line of stitching forming a seam 530 joins the fastener strip 528 to the fabric strip 520. This fastener strip 528 is preferably formed from a relatively soft loop fastener material, but if this fastener strip 528 tends to roll toward the skin during usage, sharper edges, where the fastener strip 528 is stitched to the outer fabric 504 can irritate the wearer's stomach or abdominal area causing discomfort. By employing the fabric strip 520, the tendency of the front edge of the undergarment to roll inward will be reduced or eliminated.

Fastener tabs 526 at the corners of the rear edge of the undergarment 500 are intended to grip the fastener strip 528 when the protective undergarment 500 is worn. The fastener strip 528 extends between opposite edges of the undergarment 500 to provide a very large amount of adjustability to account for the varying sizes of the wearer's of this protective undergarment.

The tabs 526 have rounded corners, with no sharp edges that would irritate the wearer's skin. The construction of these tabs 526 will be subsequently discussed in greater detail.

FIG. 12 is a view of the absorbent pad 516 that can be mounted in the pocket 512. In FIG. 12, this pad is shown prior to being folded in a tri-folded configuration for insertion into the pocket 512 as shown in FIGS. 9 and 11. This pad has a central section 534 formed of a fluid absorbent material.

Central section 534 is thicker than the other sections. Central section 534 is joined at opposite ends to side sections 536 by strips 532, which extend between the top and bottom of the pad. In use the side sections 536 are folded beneath the central pad section 534, so that the folded pad can be inserted into the pocket 512 with the absorbent central pad section 534 exposed to the wearer's pubic area. The side sections 536 are also fabricated of fluid absorbent material. The two strips 532, which are stitched between central section 534 and corresponding side sections 536, are fabricated or a fluid resistant or waterproof material. These waterproof strips 532 form hinges that help fold the side sections 536 of the pad 516 under the central section of the pad. Hinges 532 may be constructed of a material, such as a thin sheet of polyester that does not readily absorb moisture. As shown in FIG. 11, these preferably waterproof strips or gussets 532 will form edges of the absorbent pad 516, which will be adjacent to the sides of the pocket 512. Although fluid can flow from the central pad section 534 to the folded side sections 536, located directly beneath the central pad section 534, the waterproof gusset-strips 532 will prevent or retard lateral flow of fluids. The waterproof strips 532 will therefore obstruct the passage of fluids laterally over the side edges of the pocket 512, a very desirable result.

Figure 13:
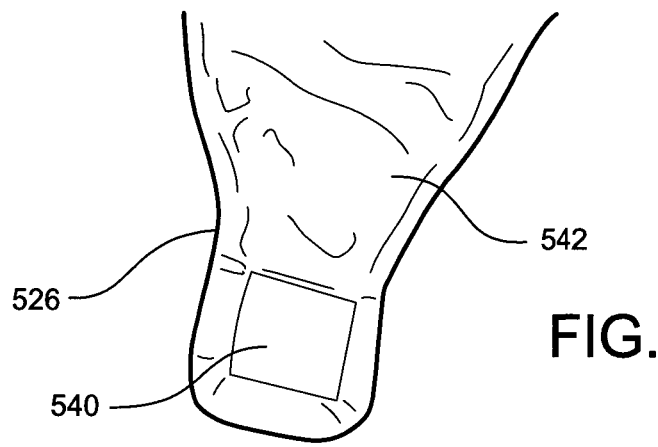
FIG. 13 is an enlarged view of a fastening tab located on the rear corners of this protective undergarment.

FIG. 13 is an enlarged view of one of the fastening tabs 526 located at the rear corners of the protective undergarment 500. These tabs 526 include a fastener 540 that can grip the fastener strip 528 on the front of the protective undergarment 500 when worn. Preferably the fastener 540 and the fastener strip 528 are hook and loop fasteners. In the embodiment depicted herein, the fastener 540 has a rectangular shape with hook fasteners, and the fastener strip 528 includes co-operable loop fasteners. The loop fasteners employed on fastener strip 528 can be chosen from commercially available materials that are smoother to the touch than co-operable hook fasteners. The fastening tabs 526 also include a section of material 542, which the hook fasteners 540 will engage when not in use, so that damage to the protective undergarment 500 will not result during handling. The hook fasteners 540 can also engage this section of material 542 to prevent tangling during handling.

Figure 14:
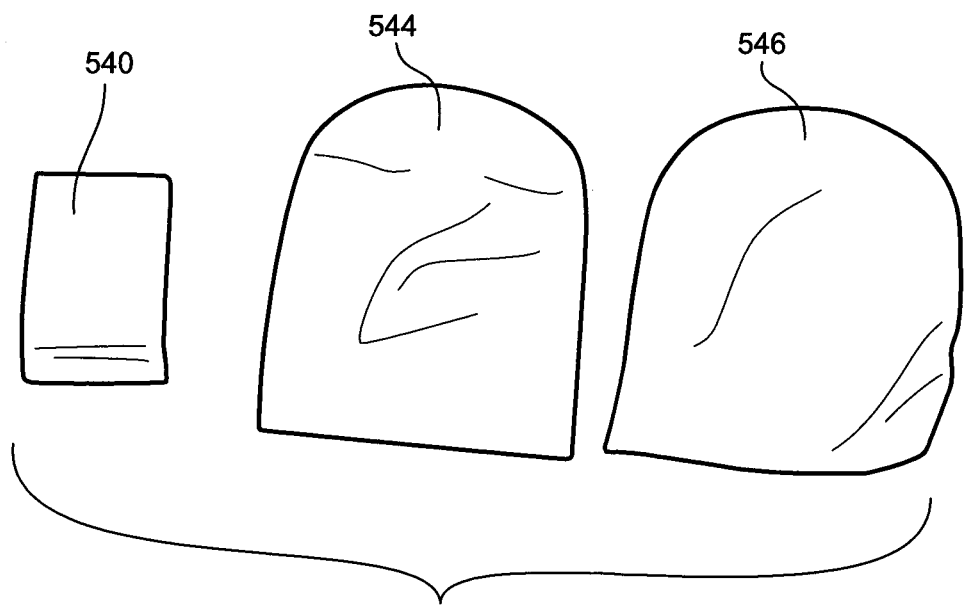
FIG. 14 shows the three principal components employed in fabricating the fastening tab of FIG. 13.

As previously discussed, the construction of this undergarment reduces the tendency of sharp edges of the fastener strip 528 to irritate the wearer's sensitive skin. The same problem must be addressed with the fastening tabs 526. To accomplish this result, the fastening tabs 526 are fabricated from three components shown in FIG. 14. A rectangular hook fastener section 540 will be attached to two layers of fabric 544 and 546, which can be the same material employed to construct the waterproof exterior 504 of the protective undergarment. Both fabric sections 544 and 546 have one smooth curved end with rounded corners, which in the final construction will form the distal or leading ends of the fastening tabs 526. These rounded ends or corners will be soft to the touch and will not irritate the wearer's skin and to the caretaker's fingers when fastening the garment shut or pulling it open.

Major steps in the fabrication of the fastening tabs 526 are shown in FIGS. 15A-15F. In the first step shown in FIG. 15A, the rectangular hook fastener section 540 is placed on one of the fabric sections 544, and the curved or rounded section 548 is folded partially over the hook fastener 540. This will cover one edge of the hook fastener 540 and this covered end will eventually form the distal edge of the hook fastener 540. It is this distal edge that, if exposed, would tend to scrape the wearer causing the most irritation.

Figure 15A:
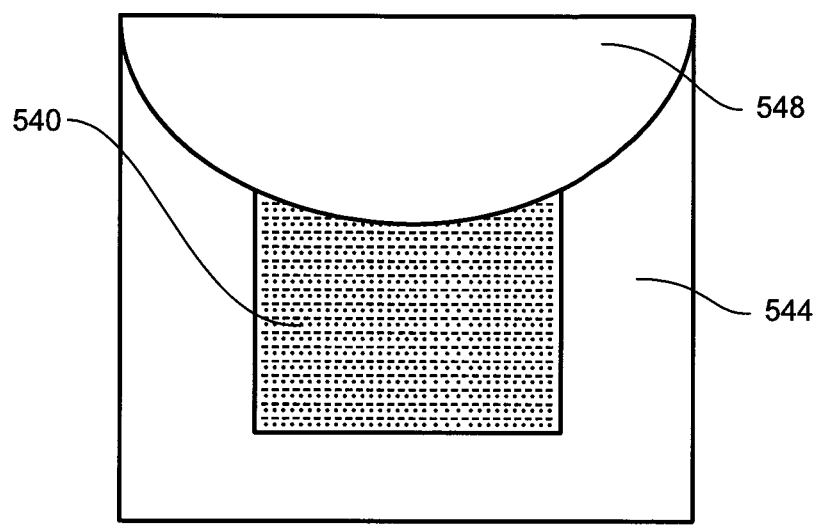
FIGS. 15A-15F show the main fabrication steps in constructing the fastening tab of FIG. 13 in a manner so that hook fasteners will not be exposed so as to avoid irritation to the wearer.
Figure 15B:
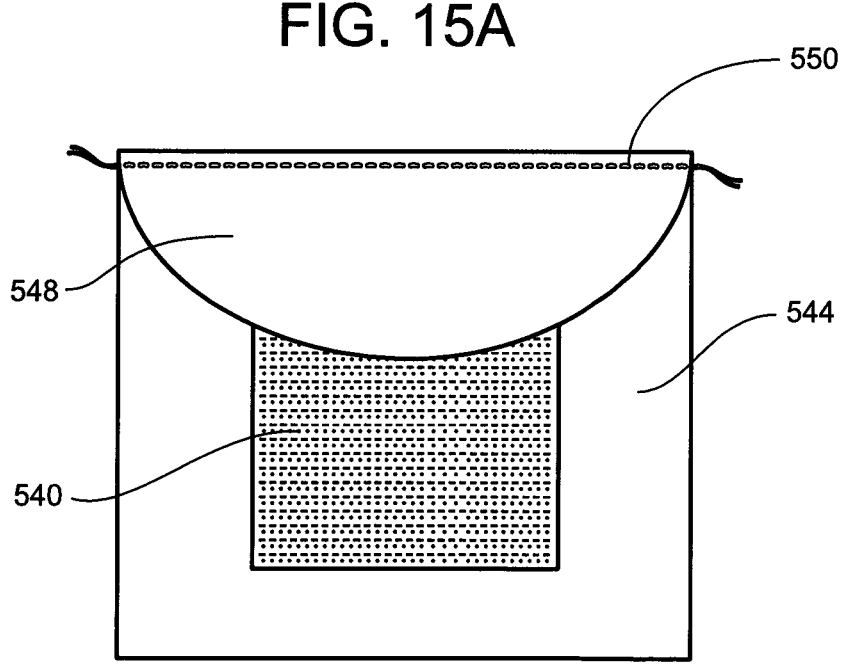
Figure 15C:
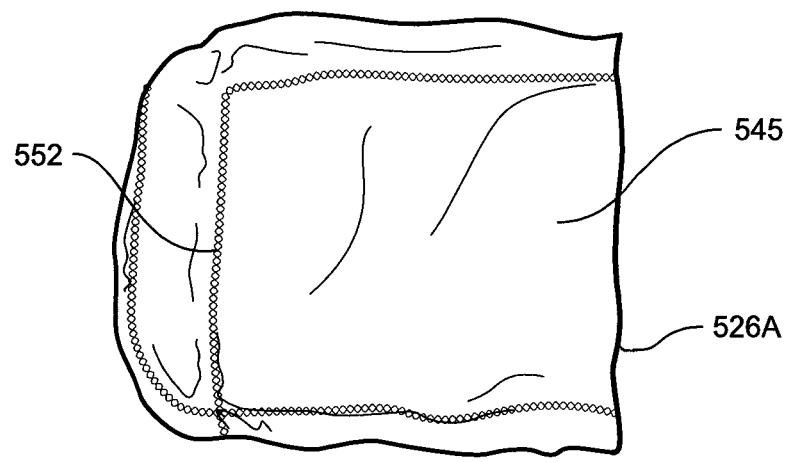

As shown in FIG. 15B, a seam 550 is stitched adjacent the folded edge of the curved section 548 of the fabric layer 544. This seam 550 extends through two folded layers of fabric 544 and through the hook fastener 540 to enclose the front edge of the hook fastener 540 between two layers of fabric. After the hook fastener 540 is secured in this manner, the curved section 548 is then folded back toward its original flat configuration. This will leave a ridge 552 shown in FIG. 15C. The stitched distal edge of hook fastener 540 will be trapped between two folds of fabric 544 to form this ridge 552, and this rectangular hook fastener edge will thus be surrounded by softer fabric and can cause no irritation to the wearer. The other fabric section 546 can now be joined to the subassembly shown in FIG. 15B by stitching around the curved sections of the two layers and along adjacent edges to form a interim sandwich configuration 545. The rectangular edge of this sandwich 545 is not stitched and the two fabric layers 544 and 546 are not attached along this edge during the step illustrated in FIG. 15C. The sandwich assembly 545 shown in FIG. 15C includes the primary materials for forming a fastening tab 526, but since this subassembly in not in its final shape it can be referred to as an interim tab assembly 526A.

Figure 15D:
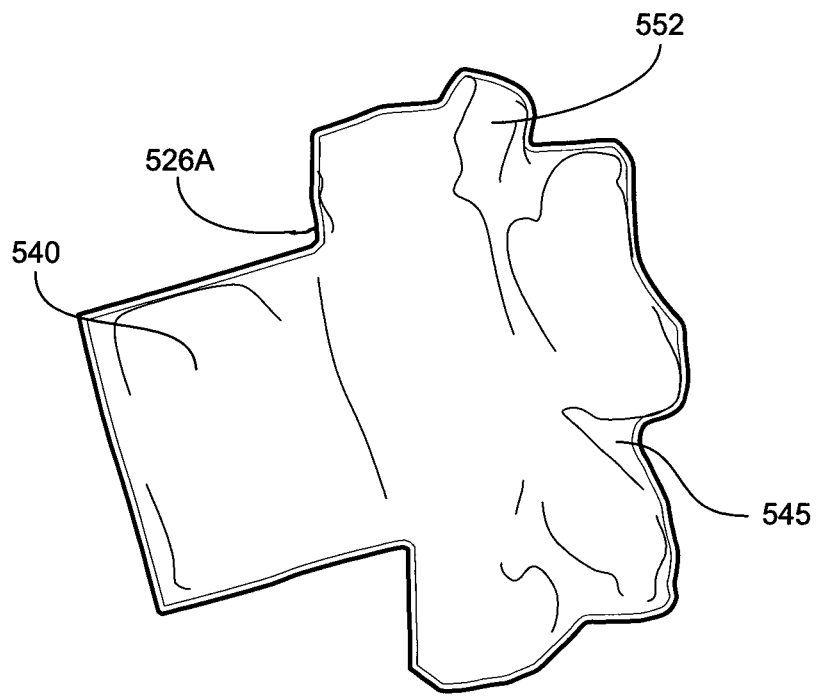
Figure 15E:
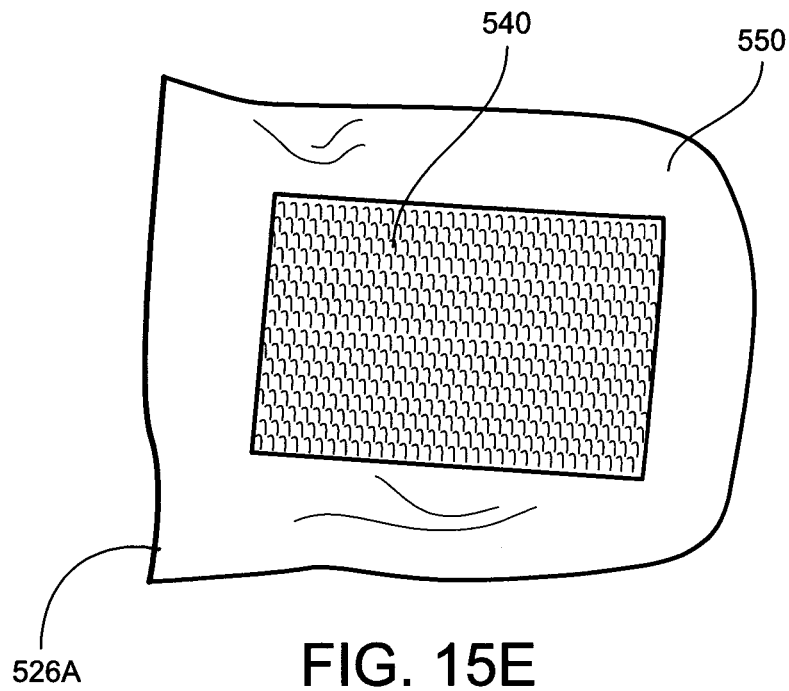
Figure 15F:
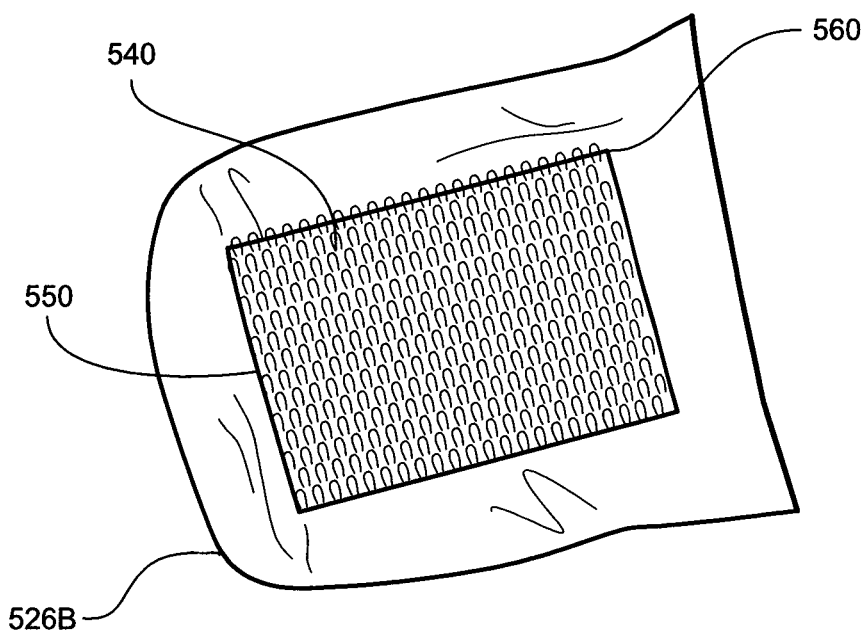

The next step in fabricating a final fastener tab assembly 526 is to reverse the two partially stitched fabric layers 544 and 546 to expose the working portions of hook fastener 540. This step is shown in FIG. 15D. The sandwich 545 is reversed by pulling the free edge of the two fabric layers 544 and 546 backward so that hook fastener 540 is exposed. FIG. 15D represents partial completion of this reversing step. FIG. 15E shows the completion of this reversing step with the hook fastener 540 exposed, except for the front edge which is secured by seam 550 and is covered by fabric layer 544 along the ridge 552, which is now located between the two fabric layers 544 and 546 in the configuration shown in FIG. 15E. Notice that in this interim configuration the hook fastener 540 is still not secured along three edges because it must still be pulled outward from its point of end attachment. The next step in the fabrication of this fastening tab is shown in FIG. 15F, which shows stitch 560, which now secures the remaining edges of the hook fastener 540. Stitch 560 extends though both layers of fabric 544 and 546 forming a final tab subassembly 526B, which can subsequently be stitched to the protective undergarment to form the final fastening tab 526 as shown in FIG. 13. In this fastening tab 526, the edges of the hook fastener 540 are now surrounded by regular stitching 550 and cross stitching 560, but more importantly these hook fastener edges are no longer in a position to irritate or scrape the wearer's skin or fingers. The distal or front edge of the hook fastener 540, which will cause the most irritation is now completely covered with a curved or rounded end of the tab extending beyond this front edge of the hook fastener. Borders also extend beyond the three remaining edges so that the hook fastener and its substrate cannot cause irritation to a wearer. These manufacturing steps are not limited to curved ends. Square and rectangular or other shaped tabs can be fabricated in this manner.

FIGS. 17A-17G show other methods of fabricating a hook fastener attachment mechanism that can be used with a protective undergarment that will provide even greater protection against irritation, scratching or discomfort from abrasive portions of a hook fastener, especially the corners of such a fastener. Although attachment of a hook fastener is demonstrated in FIGS. 17A-17G, it should be understood that similar problems can be encountered with a loop fastener, although hook fasteners are more abrasive, and this method is more critical when used with hook fasteners. The method shown in FIG. 17A-17G will provide sufficient protection against abrasive surfaces, that plastic hook fasteners, which have heretofore been considered too abrasive for use on protective undergarments can now be employed. The stronger gripping strength provided by plastic hook fasteners thus permits fabrication of undergarment configurations that were previously impractical because prior art hook and loop fasteners were considered ineffective.

Figures 17A, 17B:
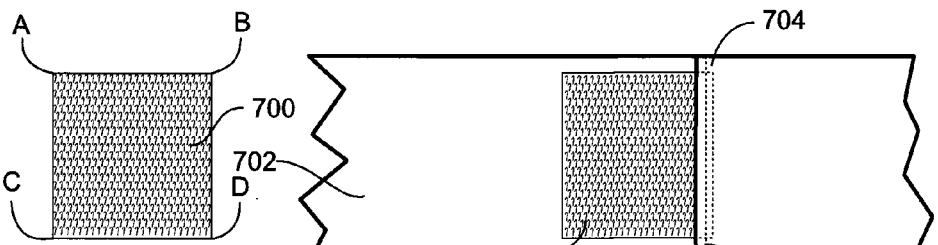
FIG. 17A is a view of a square of hook fastener.
FIG. 17B shows the attachment of one end of the hook fastener square of FIG. 16A to a strip of material by first overlapping one edge of the material over the hook fastener square and then stitching.

FIG. 17A shows a square hook fastener segment 700 that can be attached to a fabric by this method. Square hook fastener segment 700 has four corners A-D that are especially abrasive and uncomfortable when exposed to sensitive areas of a baby or an adult. Although not limited to a specific size, this method is suitable for use with square hook fasteners 700 that are one inch squares.

FIG. 17B shows a first step in attaching the hook fastener 700 to a strip of fabric or other material 702. This other material can be a natural fabric, such as cotton, a waterproof fabric, or hook fastener segments 700 can be attached to a strip of loop fastener material. One edge of the hook fastener 700 is first attached to the material strip 702 by folding a section 704 into overlapping relationship with that first hook fastener edge. The overlying section 704 is then stitched to the hook fastener 700 along seam 706.

Figure 17C:
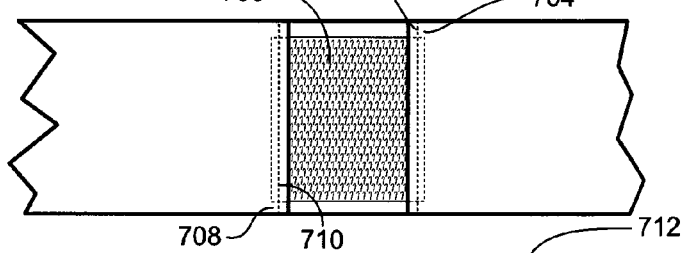
FIG. 17C shows the attachment of the square of hook fastener along the opposite side by overlapping the material over the opposite side and then stitching. Since material overlaps the hook fastener square on opposite sides, all four sharp corners of the hook fastener are now covered by the material.

All four corners A-D can be covered by folding another section 708 of the underlying material 702 over the opposite edge of the hook fastener square 700 as shown in FIG. 17C. Overlying section 708 is then stitched to the second edge of hook fastener square 700 along seam 710, which is parallel to the opposite seam 706. With overlying sections 704 and 708 stitched in this manner, all four corners A-D of the hook fastener square 700 are now sandwiched between two layers of material and these corners are covered so that sensitive skin cannot be exposed to all four hook fastener corners A-D, no matter where the hook fastener is used in an underlying protective garment.

Figure 17D:
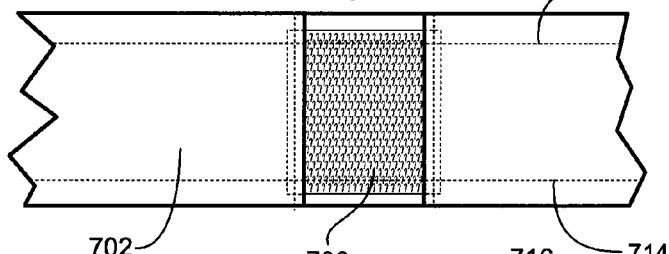
FIG. 17D shows a first alternate step in which continuous seams, such as interlocking seams secure the top and bottom edges of the hook fastener square to the strip of material.
Figure 17E:
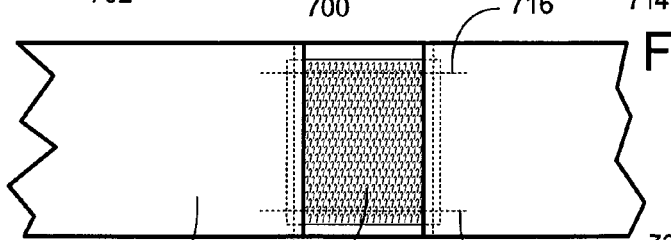
FIG. 17E shows a second alternate step in which a short seam or dart extends along the top and bottom edges of the hook fastener square.

The top and bottom edges of the hook fastener square 700 are still exposed in the step represented by FIG. 17C, but these edges are not nearly as abrasive or sharp as the corners AD. These top and bottom exposed edges can still be restrained or covered in several different ways to add further protection against abrasion or discomfort. FIG. 17D shows that seams 712 and 714 extending between opposite ends of the fabric 702 can be positioned so that the hook fastener square 700 is stitched to the fabric along the seams 712 and 714. This approach is especially suitable when the fabric strip 702 is stitched to another layer of fabric, such as cuff in a protective undergarment. FIG. 17E shows another version in which seams 716 and 718 do not extend between opposite ends of the fabric strip 702. The length of seams 716 and 718 is just sufficient to extend over the top and bottom of the hook fastener square 700.

Figures 17F, 17G:
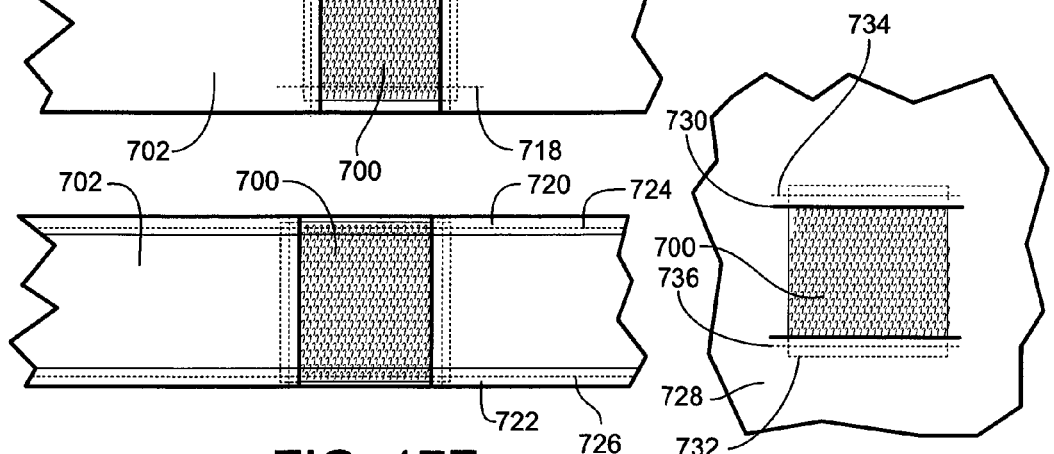
FIG. 17F shows a third alternate step in which the upper and lower edges of the material overlap the hook fastener square and are stitched thereto.
FIG. 17G shows another embodiment in which only short sections of the primary fabric are folded into overlapping relationship to the hook fastener member to form a dart.

FIG. 17F shows an alternate approach that will provide even greater coverage of the hook fastener square 700. Here, not only the corners A-D, but the four sides or edges of the hook fastener square 700 are covered by folded layers of the fabric strip 702. A top fold 720 and a bottom fold 722 along the top and bottom edges of the fabric strip overlap the top and bottom edges of the hook fastener square 700. Seams 724 and 726 then stitch the folds 720 and 722 to the hook fastener square 700.

FIGS. 17B-17F demonstrate the attachment of a single hook fastener segment 700 to a fabric strip 702. It should be understood that multiple hook fastener segments 700 can be stitched side by side to a longer strip of material 702. Multiple hook fastener segments 700 can be fabricated in this manner and individual hook fastener segments can then but cut from the longer fabric strip and attached to protective undergarments for a number of different purposes. For example, waist fastener tabs can be fabricated in this manner.

FIG. 17G shows another manner of attaching a hook fastener 700 to a fabric that need not be in the shape of an elongated strip, such as that shown in FIGS. 17B-17F. In the embodiment of FIG. 17G, small sections 730 and 732 of a larger piece of fabric are folded over opposite edges of a hook fastener square 700. A top overlying section 730 is first folded over the top edge of the hook fastener 700, and then stitched along seam 734. Then the lower fold 732 is formed and stitched along seam 736 to form a dart. The approach of FIG. 17G will be especially for use in attaching fasteners, such as hook fastener squares 700 to the back side of a removable sling, as will be subsequently discussed in greater detail. The fasteners of FIG. 17A-17G can be substituted for the fasteners shown in FIGS. 15A-15F to provide additional protection from sharp edges and corners, especially for hook fasteners.

Figure 18:
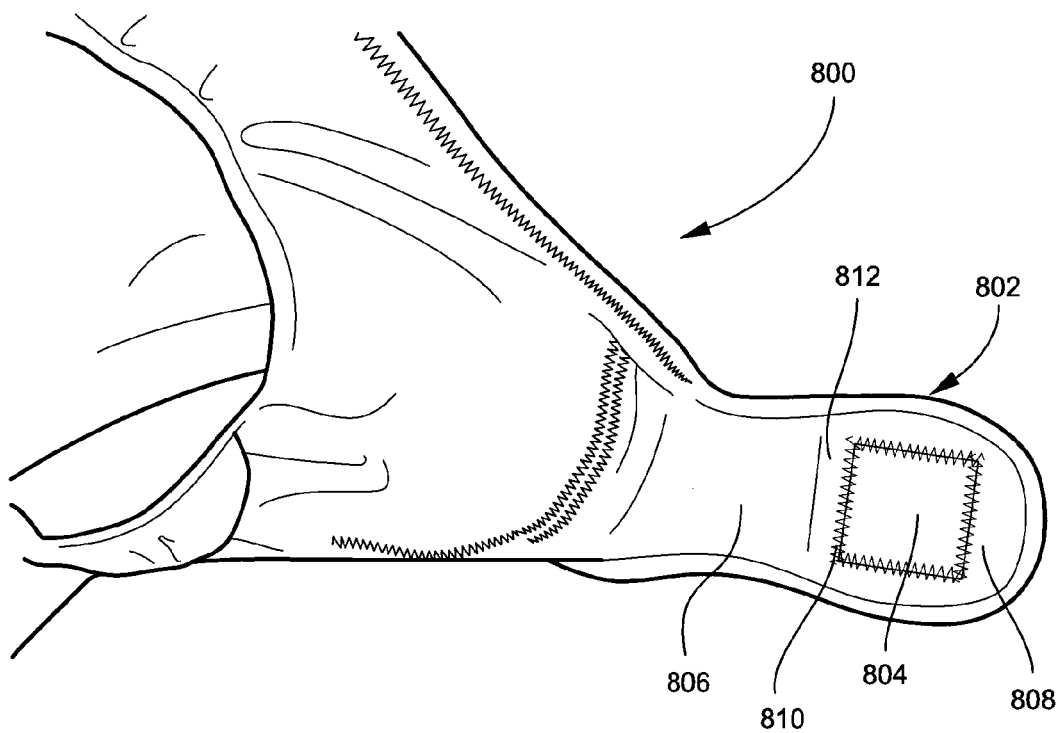
FIG. 18 is a view of a fastener tab for use in securing the undergarment around the waist of a user in which overlapping folds are formed as generally in FIGS. 17A-17G, and in which a loop fastener is employed to close the tab during washing or when not in use.

FIG. 18 shows a first example demonstrating the use of one of the methods shown in FIGS. 17A-17B. A protective undergarment 800 of the type employing a sling includes a tab 802 for securing the undergarment around the waist. The tab 802 includes a primary fastener 804 in the form of a hook fastener square fabricated in accordance with FIGS. 17B-17D. This embodiment also includes a loop fastener 806 located adjacent to the hook fastener square 804. The tab 802 is fabricated by stitching the components to an underlying material, and then turning the subassembly inside out in the same manner shown in FIGS. 15C-E in an earlier embodiment. In this embodiment, both the hook fastener 804 and the loop fastener 806 are stitched to a fabric, such as cotton, that will shrink when washed. The hook fastener square 804 is stitched by forming overlapping folds 808 and 810, which correspond to folds 704 in FIG. 17B and fold 708 in FIG. 17C. These folds 808 and 810 will cover all four corners of the hook fastener square 804. The top and bottom edges can be stitched using an overlocking seam or some other seam to completely secure the hook fastener square 804 to the underlying material. The loop fastener 806 formed adjacent the hook fastener 804 is used so that the tab 802 can be closed when the garment is washed. The hook fastener segment 804 will engage the loop fastener 806 when the tab 802 is closed so that the hook fastener 804 will not abrade or damage the protective undergarment during washing. This tab is fabricated so that the use of a shrinkable material, such as cotton, will tend to close the tab 802, even when the user does not fold the hook fastener 804 over into engagement with the loop fastener 806. A section of shrinkable cotton 812 is left between the hook fastener 804 and the loop fastener 806. As this section 812 shrinks, it will cause the hook fastener 804 to naturally bend over relative to the loop fastener 806, so that the two fasteners will tend to naturally close when not in use.

Figure 18A:
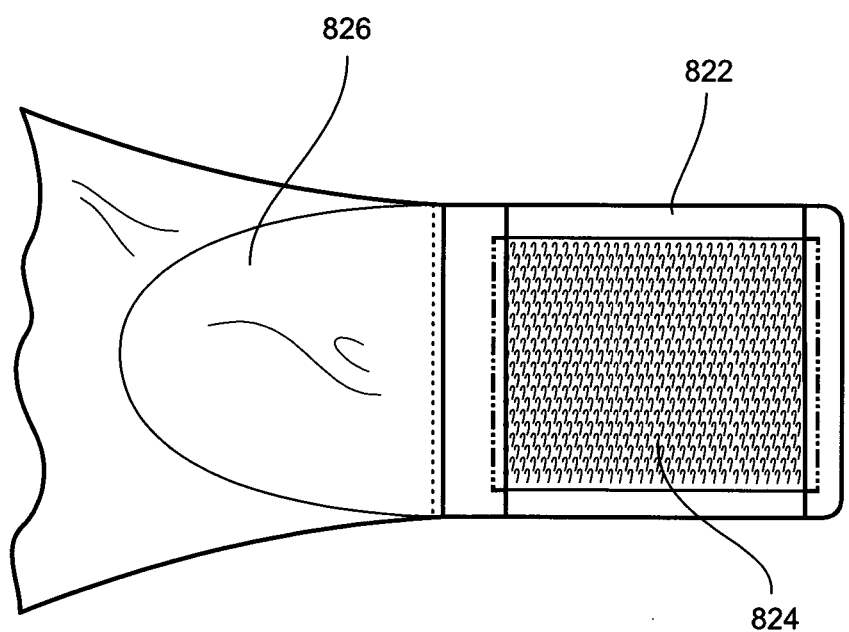
FIG. 18A shows a tab, which can be used on the same garment, but which has a different shape.

FIG. 18A shows an alternate view of a tab 822 that can be substituted for the tab 802 shown in FIG. 18. This tab 822 has a more rectangular configuration. The hook fastener 824 is rectangular but the four corners are covered by folds at the opposite ends. The covered portions of the hook fastener 824 are shown in phantom. A loop fastener 826, adjacent hook fastener 824 allows the tab 822 to be folded into a configuration in which it will not damage other portions of the garment during cleaning.

FIGS. 19A and 19B show another use of a fastener attachment of the type disclosed in FIGS. 17A-G. FIGS. 19A and 19B show the back side of a detachable pocket 900. A pocket for receiving a pad is formed on the opposite side as discussed with reference to other embodiments of pocketed slings, and fasteners 902, 904, 906 and 908 located at the four corners of the pocket 900 can be used to attach the pocket 900 to the protective undergarment, and more specifically to the fabric sling 924. In this embodiment, the hook fasteners 902, 904, 906, and 908 can comprise plastic hook fasteners of the type that will provide greater holding power than available with traditional fabric hook fasteners. This will secure the pocket 900 to the remainder of the protective undergarment and the pocket 900 will not become dislodged during normal use.

Figure 19C:
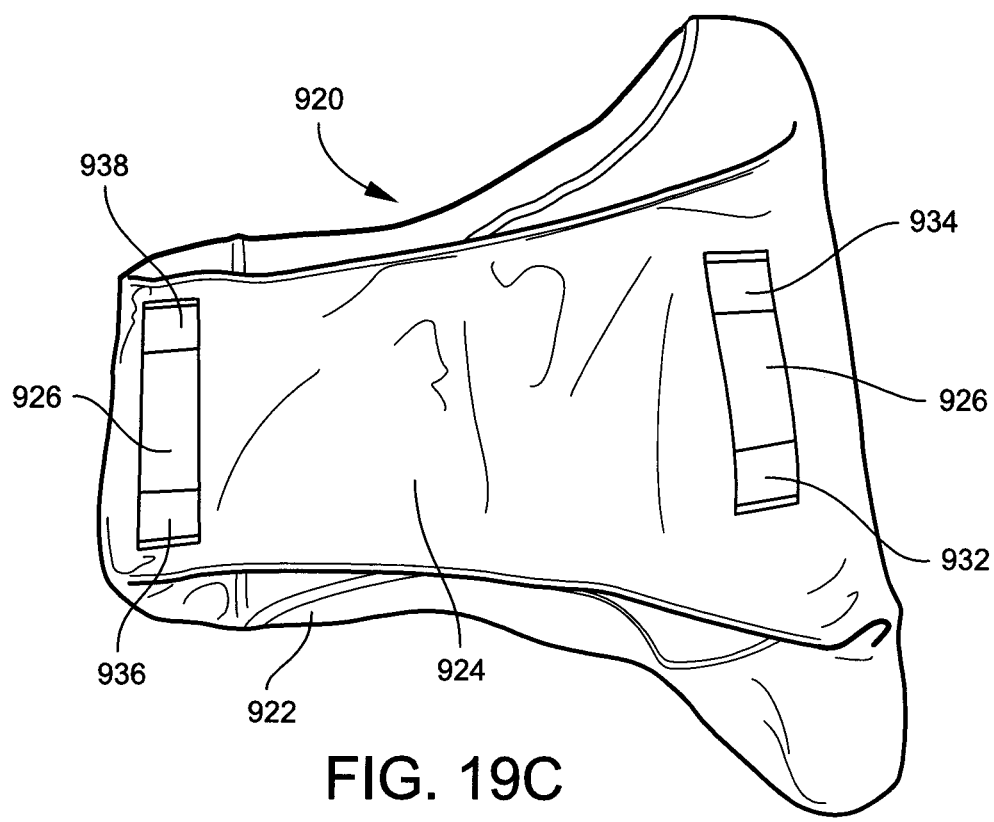
FIG. 19C is a view of an undergarment with which the sling of FIGS. 19A and 19B can be used.
Figure 19D:
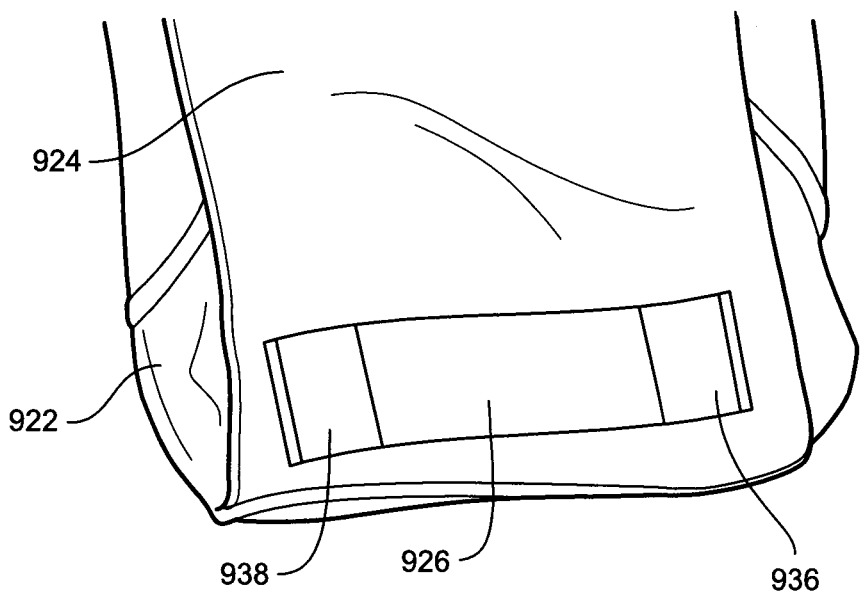
FIG. 19D is a close upon of one end of the undergarment of FIG. 19C.

The fasteners 902, 904, 906 and 908 can be secured to the detachable pocket 900 in the manner described with reference to FIG. 17G by forming a dart stitch or seam. Dart stitches or seams 910 and 912 are seen in FIG. 19A. These seams are located on the most exposed surface of the fasteners 902 and 904, where abrasion will most likely occur during use or when the detachable pocket 900 is attached to the undergarment. In the embodiment of FIG. 17G folds will be formed along opposite sides of the hook fastener square, and use of this configuration for fasteners 902, 904, 906 and 908 will cover all four corners of each hook fastener. Even if a conventional stitch is used around three of the four corners, the use of a stitched overlapping fold 910 and 912 only along the most exposed edge will provide additional protection, especially for a relatively more abrasive plastic hook fastener. It should be understood that a strip of material having two hook fasteners attached in the manner of FIG. 17C-17F could also be stitched to the pocket 900. In that version, the hook fasteners would be spaced apart so that they would be on the corners of the pocket 900. Although other detachable pockets have employed hook and loop fasteners to attach a sling to an undergarment, other versions have recessed the hook or loop fasteners from the corners of the sling. However, with the overlying configuration of the present invention, the fasteners can be employed closer to the corners where they can be easily attached. The benefits of a relatively thin hook and loop fasteners can thus be more effectively realized and bulky attachment members, such as snaps can be eliminated, reducing discomfort to the wearer. It should be understood, however, that instead of employing hook fasteners, loop fasteners can be substituted on the pocket 900. FIGS. 19C and 19D show a protective undergarment 920 that can be employed with the pocket 900 of FIGS. 19A and 19B. This protective undergarment 920 includes an outer shell 922 and a fabric sling 924 attached to the outer shell 922 on at least the front and back ends of both subcomponents. The fabric sling 924 can also be attached to a conventional garment, such as a diaper or an underpant. The outer garment or shell 922 and the fabric sling 924 can be formed of the same material, or if desired from different materials. The fabric sling 924 will, however fit the groin of the wearer with stability and tightness providing both comfort and security against leakage that might escape the pocket 900. The outer garment or shell 922 can fit separately fit around the wearer's legs. Fasteners 932, 934, 936 and 938 are attached to the fabric sling 924 at each of the four corners so that the pocket 900 can be attached to the fabric sling 924. Fastener 902, 904, 906 and 908 can be attached to fasteners 932, 934, 936 and 938. It should be understood that if the fasteners on the pocket 900 are hook fasteners, then the fasteners on the fabric sling 924 will be loop fasteners and vice versa. Again to prevent abrasion or irritation to the wearer, folds can be formed on opposite sides of each fastener to cover the corners of the fasteners. In the embodiment shown in FIGS. 19C and 19D, a strip 926 containing spaced fasteners stitched to the strip 926 is in turn stitched along opposite ends of the fabric sling so that fasteners are located at each corner of the fabric sling 924. When the detachable pocket 900 is mounted on the fabric sling 924, a pocket bearing sling subassembly is formed. The pocket bearing subassembly can be easily attached to a conventional undergarment by simply stitching the fabric sling 924 to the front and rear of the conventional undergarment. In these embodiments the fasteners 932, 934, 936 and 938 need only be stitched or attached to the fabric sling 924 and need not be attached to the outer shell 932. It should be understood that any of the fastener configurations shown in FIG. 17C-170 could be used for hook fasteners 902, 904, 906, and 906.

Figure 19E:
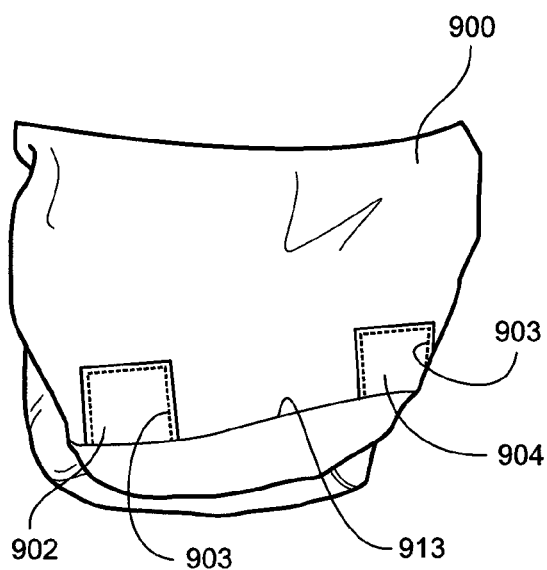
FIG. 19E is a more detailed view of the dart stitches that cover exposed edges and sides of fastener tabs on the pocket.

FIGS. 19E-191-I are more detailed views, which also illustrate some of the available options for mounting fasteners on the pocket 900. FIG. 10E shows a configuration similar to that shown in FIGS. 19A and 10B in which two hook fasteners 902 and 904 are located near the corners of the pocket 900. In this embodiment a single dart stitch 913 extends across both fasteners 902 and 904. Dart stitch 913 essentially can be formed by merging the dart stitches 910 and 912 shown in FIG. 19A. In this version the other three sides of fastener tabs 902 an 904 can be joined to the outer layer 907 by conventional stitches 903 since these sides and edges will not be as exposed.

Figure 19F:
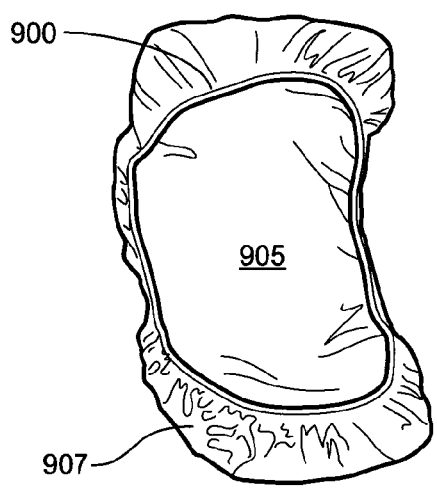
FIG. 19F shows that the pocket is formed of two fabric layers, the inner being waterproof, and dart stitches being confined to the outer layer.

FIG. 19F shows the inside of a pocket 900 showing that the pocket has two layers. Inner pocket layer 905 is waterproof or water repellant and will not permit moisture to lead from the pocket 900. The outer pocket layer 907 forming pocket 900 need not be waterproof. The dart stitches 910, 912 and 913, as well as the conventional stitches 903, extend only through the outer layer 907 and thus can be isolated from the waterproof layer 905, eliminating a potential leakage path.

Figure 19G:
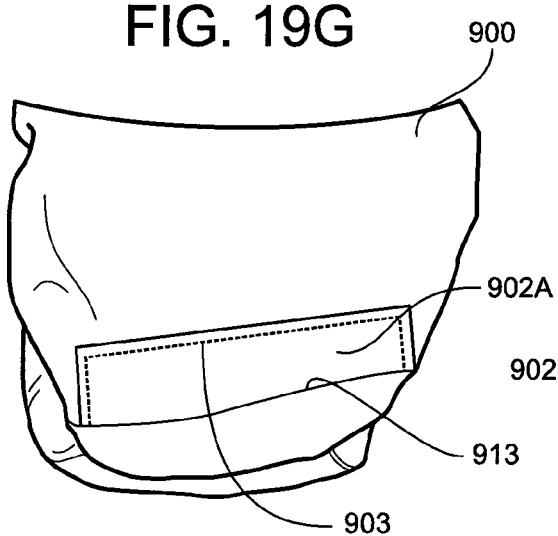
FIG. 19G shows another embodiment in which a single continuous fastener tab extends substantially across the width of the pocket.
Figure 19H:
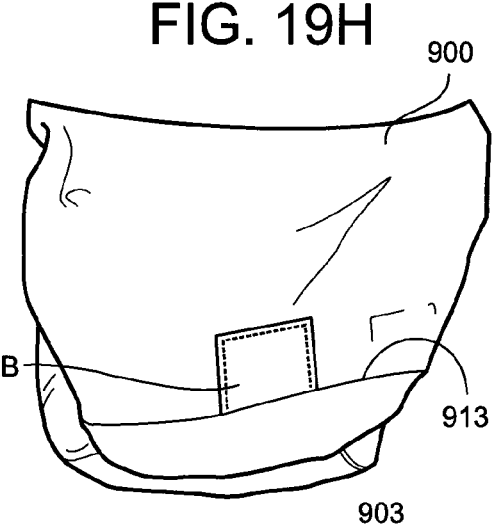
FIG. 19H shows a single fastener tab centered relative to the pocket.

FIG. 19G shows an alternate fastener tab 902A that can extend across substantially the entire width of the pocket 900 and need not be confined to the pocket corners. A single dart stitch 913 covers the most exposed side and edges of this fastener tab. A conventional stitch 903 joins the other three sides to the outer pocket layer 907. FIG. 19H shows another version in which the fastener tab 902B is not as wide as the pocket 900 and is located near its centerline. Note that the dart stitch 913 can extend beyond the fastener tab 902B, which may be preferable for manufacturing.

Figure 20A:
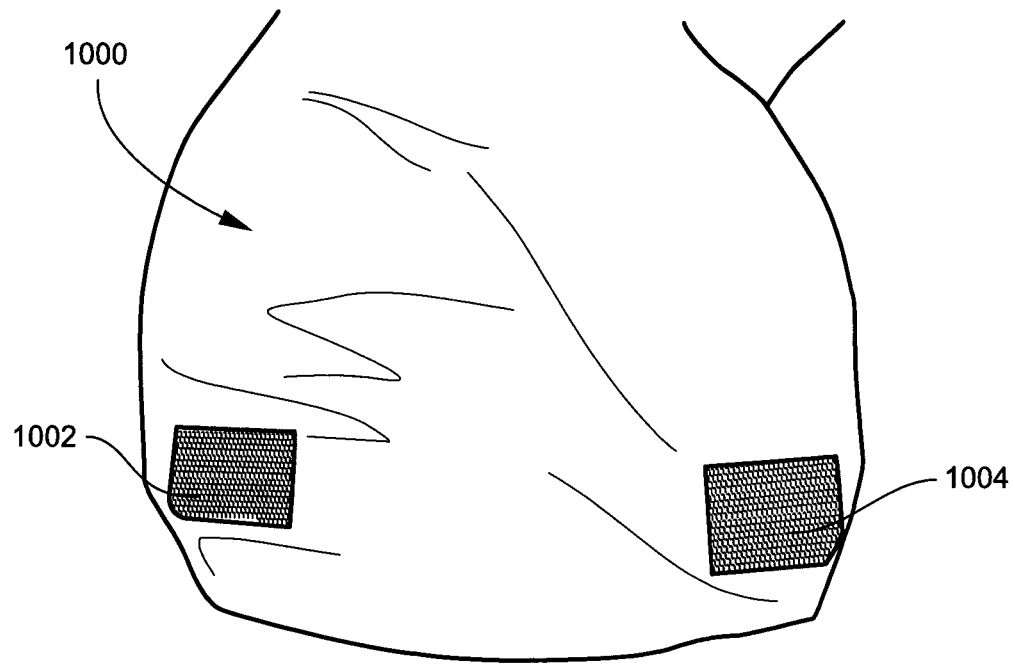
FIG. 20A is a view of another detachable sling that can be attached to and detached from a protective undergarment, one end of which is shown in FIG. 20B in which fasteners are mounted in a cuff on the undergarment.
Figure 20B:

FIG. 20A is a view of another detachable sling that can be attached to and detached from a protective undergarment, one end of which is shown in FIG. 20B in which fasteners are mounted in a cuff on the undergarment. In this embodiment a sling 1000 includes loop fasteners 1002 and 1004 attached to the exterior of the sling 1000 in much the same manner as discussed with reference to FIGS. 19A-19D. Fasteners (not shown) would also be located on the opposite end of the sling 1000. Here the loop fasteners 1002 and 1004 are secured at corners of the sling 1000 by stitches forming a dart as previously discussed. Corners, especially at the exposed edge of the loop fastener are thus shielded. Mating hook fasteners 1012 and 1014 are located on a cuff 1020 located on one end of an outer layer 1022. Cuff 1020 extends along one end of this undergarment. A cuff can also be located at the opposite end. Hook fasteners 1012 and 1014 are attached to the cuff 1020 so that all four sides and all four corners of the hook fastener are covered by either folding fabric over the hook fastener 1012 and 1014 or by stitching a border along the front edge. In any event all of the corners of the hook fasteners 1012 and 1014 are covered.

Figure 21A:
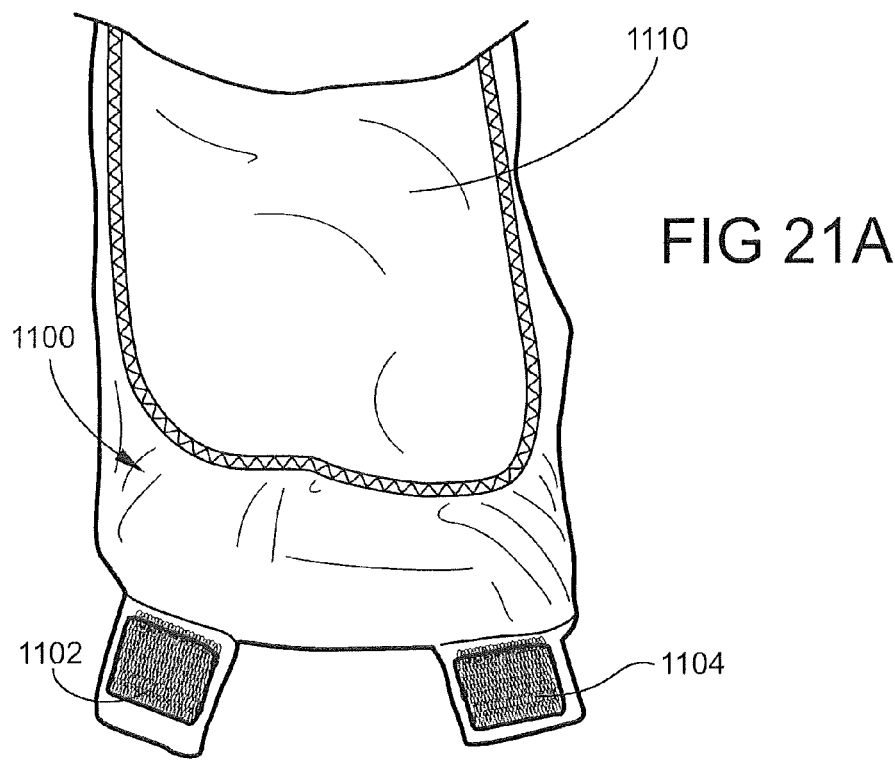
FIG. 21A is a view of another embodiment of a sling that can be attached to an outer portion of a protective undergarment by using hook and loop fasteners.
Figure 21B:
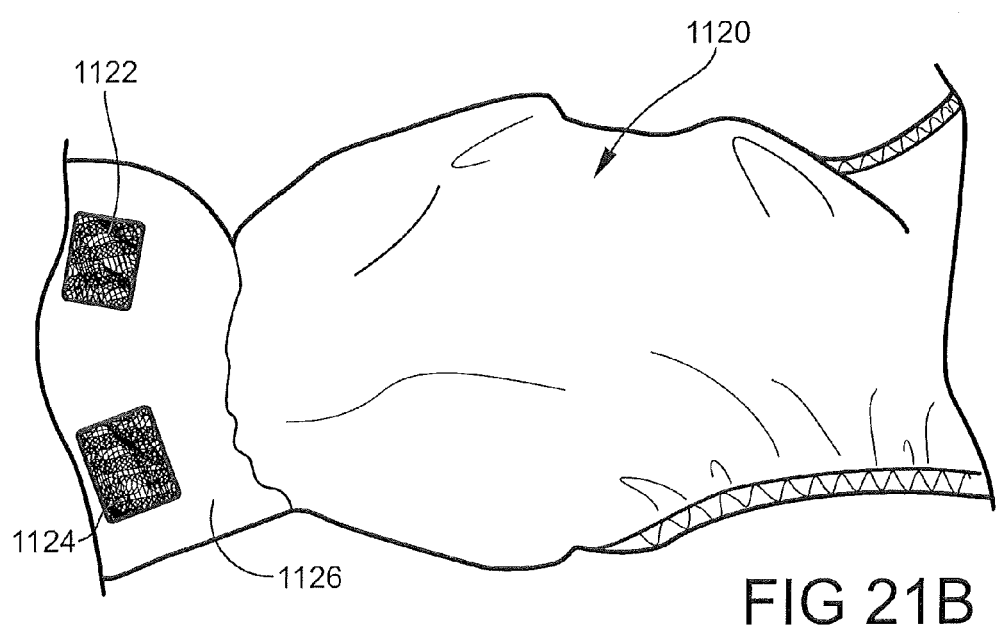
FIG. 21B shows the outer portion of the protective undergarment used with the sling shown in FIG. 21A.

The protective undergarment shown in FIGS. 21A and 21B demonstrate another method of attaching a pocketed sling 1000, in which an absorbent pad can be positioned, to an outer garment member 1120 by using hook and loop fasteners. In this embodiment the fasteners 1102 and 1104 at one end of the straps 1106 and 1108. Similar fasteners can be used at the opposite end of the sling 1000. Fasteners 1102 and 1104 can be hook or loop or a combination thereof. The fasteners 1102 and 1104 attachable to complementary hook and loop fasteners 1122 and 1124 located on the underside of a cuff 1126. The fasteners on the sling and the outer garment member 1120 can have folds that cover the corners, or since the fasteners will be on the underside of the cuff 1126, fasteners without edge protection can be employed in this embodiment.

Figure 22:
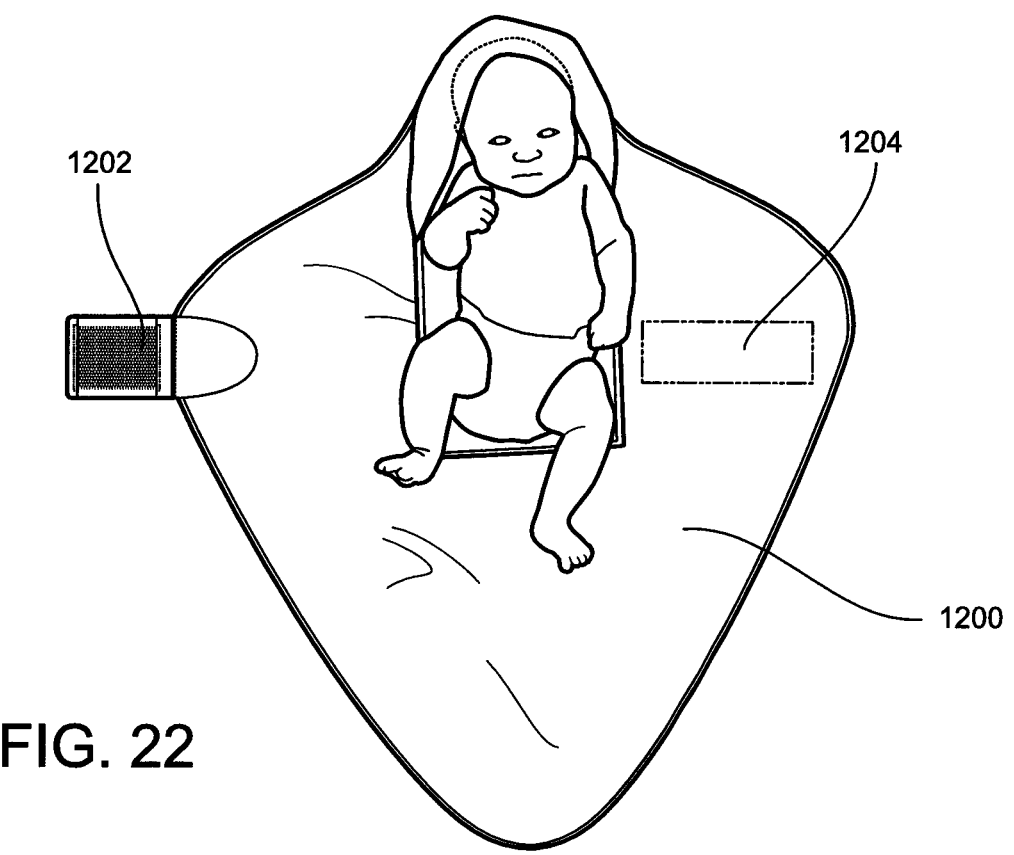
FIG. 22 is a view of an infant wrap using a tab having the same configuration as that shown in FIG. 18A.

FIG. 22 shows an embodiment in which a tab 1202, identical to tab 822 is used on a kite shape infant wrap or blanket 1200, which can be folded around an infant. A loop fastener 1204, on the opposite surface of the wrap 1200 is shown in phantom.

Numerous variations of this protective undergarment and its associated components are of course possible. One of ordinary skill in the art could make such modifications, and this invention is therefore defined by the following claims and is not limited to the details of the representative embodiments depicted herein.

What is claimed is:

1. A reusable protective undergarment comprising:
   an outer member conforming to the waist and groin of a wearer;
   a pocket member removably attached to the outer member;
   an absorbent pad insertable into and removable from the pocket member; and
   complementary hook and loop fasteners, removably attaching the pocket member to the outer member, arranged on a backside of the pocket member to attach corners of the pocket member to the outer member, each hook fastener including a rectangular hook fastener strip having abrasive sides and corners, the hook fastener strip being stitched to a fabric member, wherein dart stitches comprising overlapping portions of the fabric member are formed on opposite sides of the hook fastener strip so that the overlapping portions cover four corners of the hook fastener strip so that no abrasive corner of the hook fastener strip is exposed.

2. The protective undergarment of claim 1 wherein the outer member comprises an outer shell and a fabric sling including complementary hook and loop fastener members for removably attaching the pocket member to the fabric sling.

3. The protective undergarment of claim 1 wherein all four sides of each hook fastener strip are sandwiched between two layers of the fabric member.

4. The protective undergarment of claim 1 wherein each loop fastener includes a rectangular segment attached to a strip of fabric folded and sewn to the loop fastener such that all four corners of the rectangular segment are sandwiched between two layers of the fabric.

5. The protective undergarment of claim 4 wherein all four sides of each loop fastener are sandwiched between two layers of the fabric.

6. The protective undergarment of claim 1 wherein a cuff extends from at least one edge of the outer member, the cuff being attached to only one end of the outer member.

* * * * *